(12) United States Patent
Solem et al.

(10) Patent No.: US 7,637,946 B2
(45) Date of Patent: Dec. 29, 2009

(54) COILED IMPLANT FOR MITRAL VALVE REPAIR

(75) Inventors: Jan Otto Solem, Stetten (CH); Faisal Kalam, Anaheim, CA (US); Michael Popp, Orange, CA (US); Xiangyang Zhang, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 239 days.

(21) Appl. No.: 11/670,386

(22) Filed: Feb. 1, 2007

(65) Prior Publication Data

US 2007/0185572 A1 Aug. 9, 2007

Related U.S. Application Data

(60) Provisional application No. 60/772,984, filed on Feb. 9, 2006.

(51) Int. Cl.
*A61F 2/06* (2006.01)
(52) U.S. Cl. ...................................... 623/2.37
(58) Field of Classification Search ........ 623/2.36–2.38
See application file for complete search history.

(56) References Cited

U.S. PATENT DOCUMENTS

| | | | |
|---|---|---|---|
| 4,655,771 A | 4/1987 | Wallsten | |
| 5,064,435 A | 11/1991 | Porter | |
| 5,071,407 A | 12/1991 | Termin et al. | |
| 5,170,802 A | 12/1992 | Mehra | |
| 5,209,730 A | 5/1993 | Sullivan | |
| 5,224,491 A | 7/1993 | Mehra | |
| 5,304,131 A | 4/1994 | Paskar | |
| 5,382,259 A | 1/1995 | Phelps et al. | |
| 5,383,892 A | 1/1995 | Cardon et al. | |
| 5,390,661 A | 2/1995 | Griffith et al. | |
| 5,441,515 A | 8/1995 | Khosravi et al. | |
| 5,449,373 A | 9/1995 | Pinchasik et al. | |
| 5,496,275 A | 3/1996 | Sirhan et al. | |
| 5,531,779 A | 7/1996 | Dahl et al. | |
| 5,545,209 A | 8/1996 | Roberts et al. | |
| 5,591,197 A | 1/1997 | Orth et al. | |
| 5,607,444 A | 3/1997 | Lam | |

(Continued)

FOREIGN PATENT DOCUMENTS

EP 0955017 4/1999

(Continued)

OTHER PUBLICATIONS

Buchanan, et al., Circumferential Suture of the Mitral Annulus for Correction of Mitral Regurgitation in Dogs, Veterinary Surgery, 27:182-193, 1998.

*Primary Examiner*—Suzette J Gherbi
(74) *Attorney, Agent, or Firm*—David L. Hauser; Michael Crapenhoft

(57) ABSTRACT

An apparatus for treating a mitral valve, comprising an elongate member having a spiral shape, the elongate member having a proximal end portion and a distal end portion, an expandable proximal anchor joined to the proximal end portion of the elongate body, and an expandable distal anchor joined to the distal end portion of the elongate body. The elongate member is configured to adjust from an elongated state to a shortened state after delivery at least partially into a coronary sinus for reshaping a mitral annulus.

22 Claims, 14 Drawing Sheets

U.S. PATENT DOCUMENTS

| | | | |
|---|---|---|---|
| 5,713,949 A | 2/1998 | Jayaraman | |
| 5,817,126 A | 10/1998 | Imran | |
| 5,876,433 A | 3/1999 | Lunn | |
| 5,891,108 A | 4/1999 | Leone et al. | |
| 5,935,081 A | 8/1999 | Kadhiresan | |
| 5,954,761 A | 9/1999 | Machek et al. | |
| 5,961,545 A | 10/1999 | Lentz et al. | |
| 5,980,522 A | 11/1999 | Koros et al. | |
| 6,006,122 A | 12/1999 | Smits | |
| 6,013,854 A | 1/2000 | Moriuchi | |
| 6,051,020 A | 4/2000 | Goicoechea et al. | |
| 6,077,296 A | 6/2000 | Shokoohi et al. | |
| 6,093,203 A | 7/2000 | Uflacker | |
| 6,110,100 A | 8/2000 | Talpade | |
| 6,123,699 A | 9/2000 | Webster, Jr. | |
| 6,161,029 A | 12/2000 | Spreigl et al. | |
| 6,161,543 A | 12/2000 | Cox et al. | |
| 6,165,169 A | 12/2000 | Panescu et al. | |
| 6,168,619 B1 | 1/2001 | Dinh et al. | |
| 6,171,329 B1 | 1/2001 | Shaw et al. | |
| 6,210,432 B1 | 4/2001 | Solem et al. | |
| 6,368,348 B1 | 4/2002 | Gabbay | |
| 6,402,781 B1 | 6/2002 | Langberg et al. | |
| 6,537,314 B2 | 3/2003 | Langberg et al. | |
| 6,569,198 B1 | 5/2003 | Wilson et al. | |
| 6,629,534 B1 | 10/2003 | St. Goar et al. | |
| 6,656,221 B2 | 12/2003 | Taylor et al. | |
| 6,676,702 B2 | 1/2004 | Mathis | |
| 6,706,065 B2 | 3/2004 | Langberg et al. | |
| 6,709,456 B2 | 3/2004 | Langberg et al. | |
| 6,764,510 B2 | 7/2004 | Vidlund et al. | |
| 6,790,231 B2 | 9/2004 | Liddicoat et al. | |
| 6,800,090 B2 | 10/2004 | Alferness et al. | |
| 6,810,882 B2 | 11/2004 | Langberg et al. | |
| 6,890,353 B2 | 5/2005 | Cohn et al. | |
| 6,908,478 B2 | 6/2005 | Alferness et al. | |
| 6,989,028 B2 | 1/2006 | Lashinski et al. | |
| 6,997,951 B2 * | 2/2006 | Solem et al. | 623/2.37 |
| 7,011,682 B2 | 3/2006 | Lashinski et al. | |
| 7,044,967 B1 | 5/2006 | Solem et al. | |
| 7,090,695 B2 | 8/2006 | Solem et al. | |
| 7,144,363 B2 | 12/2006 | Pai et al. | |
| 7,192,443 B2 * | 3/2007 | Solem et al. | 623/2.37 |
| 2001/0018611 A1 | 8/2001 | Solem et al. | |
| 2002/0019660 A1 | 2/2002 | Gianotti et al. | |
| 2002/0087173 A1 | 7/2002 | Alferness et al. | |
| 2002/0111647 A1 | 8/2002 | Khairkhahan et al. | |
| 2002/0183838 A1 | 12/2002 | Liddicoat et al. | |
| 2002/0188170 A1 | 12/2002 | Santamore et al. | |
| 2003/0078465 A1 | 4/2003 | Pai et al. | |
| 2003/0083538 A1 | 5/2003 | Adams et al. | |
| 2003/0120341 A1 | 6/2003 | Shennib et al. | |
| 2003/0135267 A1 * | 7/2003 | Solem et al. | 623/1.18 |
| 2003/0171806 A1 | 9/2003 | Mathis et al. | |
| 2003/0204138 A1 | 10/2003 | Choi | |
| 2004/0073302 A1 | 4/2004 | Rourke et al. | |
| 2004/0102840 A1 | 5/2004 | Solem et al. | |
| 2004/0102841 A1 | 5/2004 | Langberg et al. | |
| 2004/0116809 A1 | 6/2004 | Webler et al. | |
| 2004/0133220 A1 | 7/2004 | Lashinski et al. | |
| 2004/0138744 A1 | 7/2004 | Lashinski et al. | |
| 2004/0176840 A1 | 9/2004 | Langberg et al. | |
| 2004/0254600 A1 | 12/2004 | Zarbatany et al. | |
| 2005/0004667 A1 * | 1/2005 | Swinford et al. | 623/2.36 |
| 2005/0043792 A1 | 2/2005 | Solem et al. | |
| 2005/0060030 A1 | 3/2005 | Lashinski et al. | |
| 2005/0080483 A1 | 4/2005 | Solem et al. | |
| 2005/0096740 A1 | 5/2005 | Langberg et al. | |
| 2005/0177228 A1 * | 8/2005 | Solem et al. | 623/2.36 |
| 2005/0187620 A1 * | 8/2005 | Pai et al. | 623/2.37 |
| 2005/0222678 A1 | 10/2005 | Lashinski et al. | |
| 2006/0116756 A1 | 6/2006 | Solem et al. | |
| 2006/0116757 A1 | 6/2006 | Lashinski et al. | |
| 2006/0129051 A1 | 6/2006 | Rowe et al. | |
| 2006/0184230 A1 | 8/2006 | Solem et al. | |
| 2006/0276890 A1 | 12/2006 | Solem et al. | |
| 2007/0038297 A1 | 2/2007 | Bobo et al. | |
| 2007/0073391 A1 * | 3/2007 | Bourang et al. | 623/2.11 |
| 2007/0173926 A1 | 7/2007 | Bobo et al. | |

FOREIGN PATENT DOCUMENTS

| | | |
|---|---|---|
| WO | WO 96/34211 | 10/1996 |
| WO | WO 98/51365 | 11/1998 |
| WO | WO 99/44534 | 9/1999 |
| WO | WO 00/18320 | 4/2000 |
| WO | WO 01/00111 | 1/2001 |
| WO | WO 01/89426 A1 | 11/2001 |
| WO | WO 02/00099 | 3/2002 |
| WO | WO 02/060352 | 8/2002 |
| WO | WO 02/076284 A2 | 10/2002 |
| WO | WO 02/078576 A2 | 10/2002 |
| WO | WO 03/037171 A2 | 5/2003 |
| WO | WO 03/055417 | 7/2003 |
| WO | WO 2004/019816 A2 | 3/2004 |
| WO | WO 2004/045463 A2 | 6/2004 |

* cited by examiner

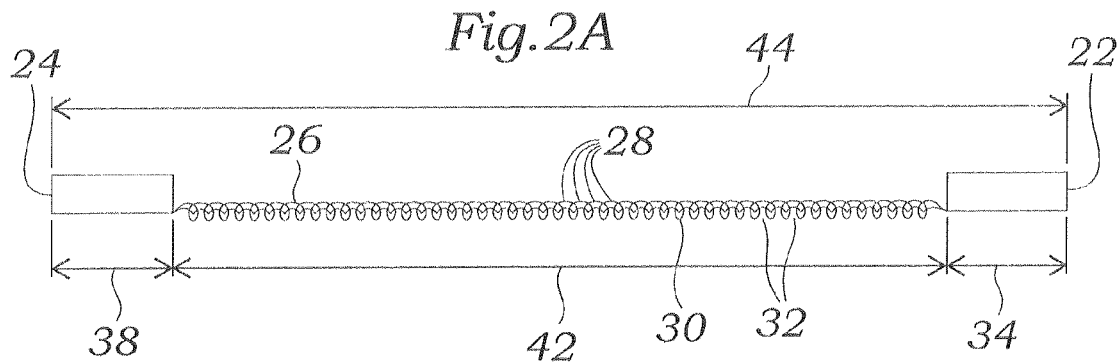
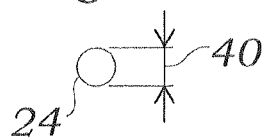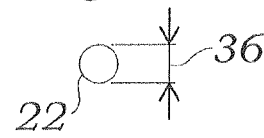
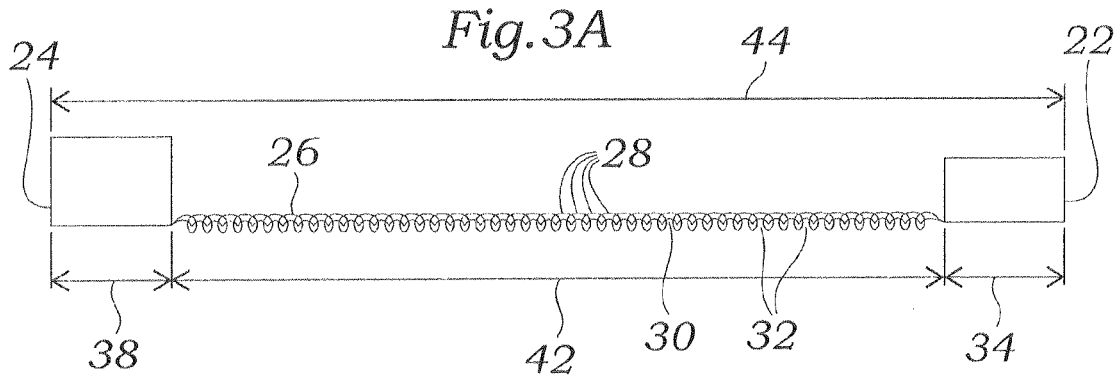
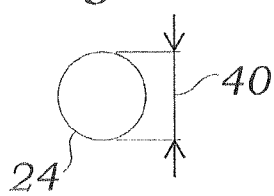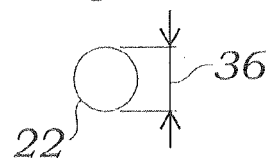
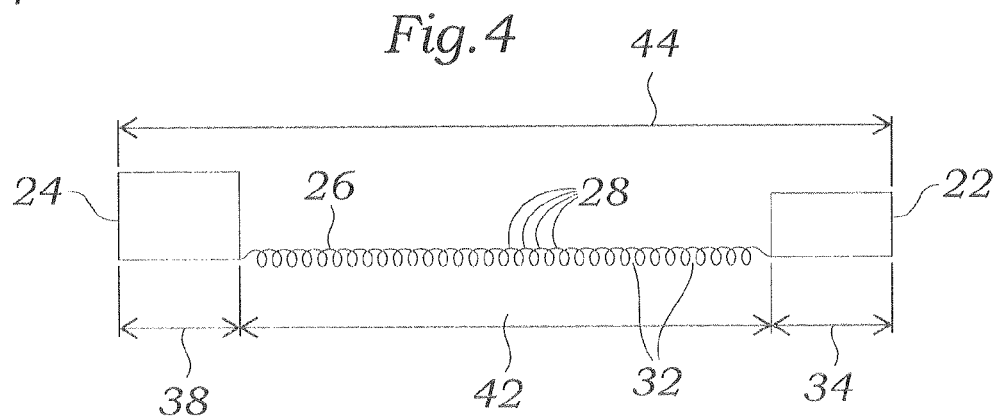

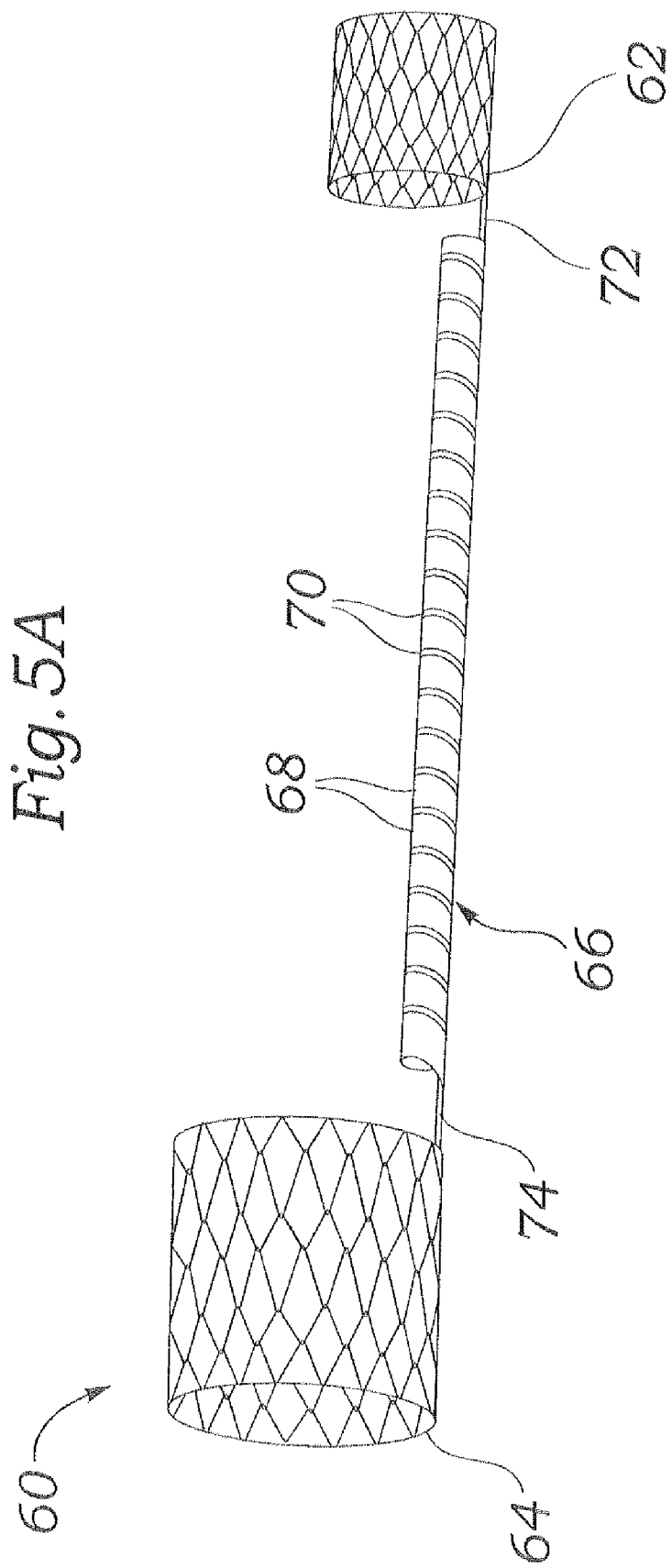

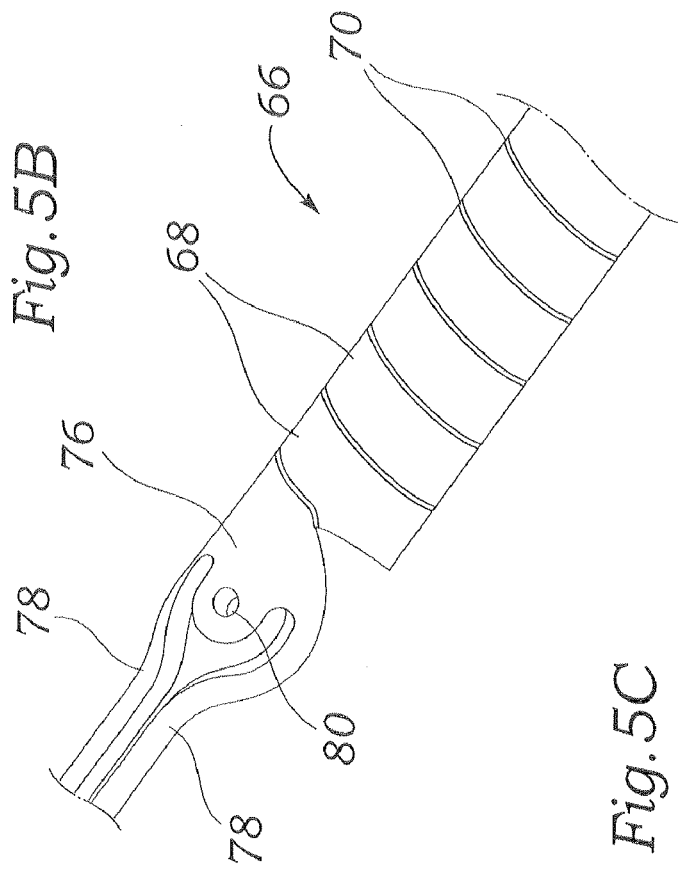
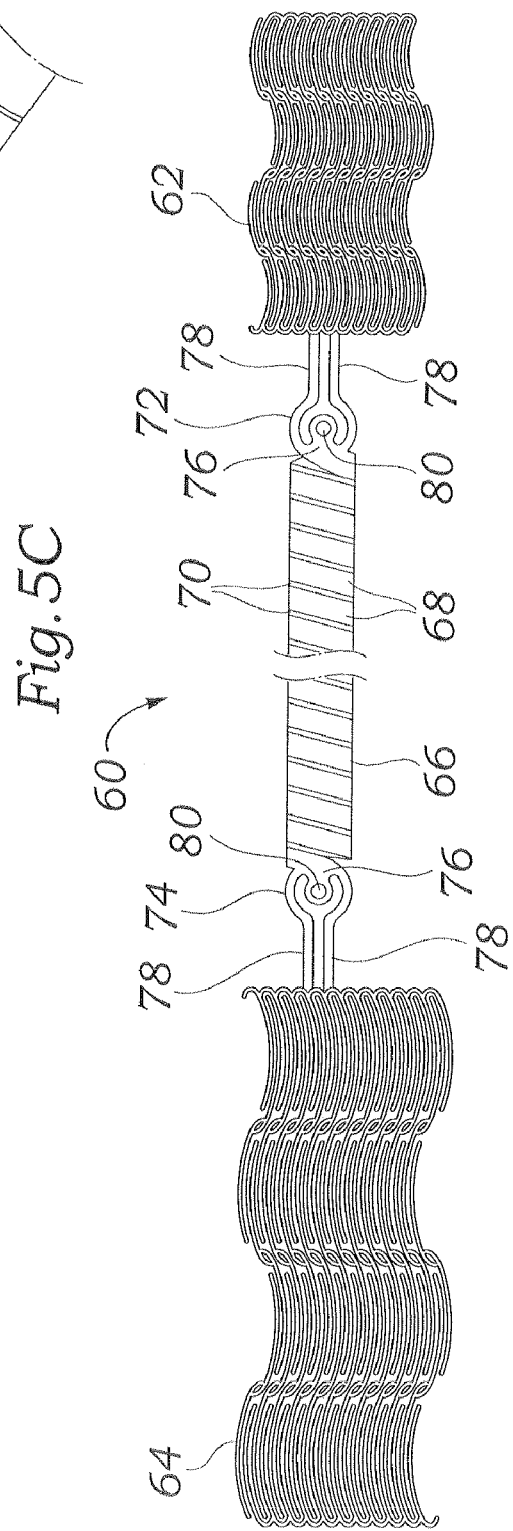

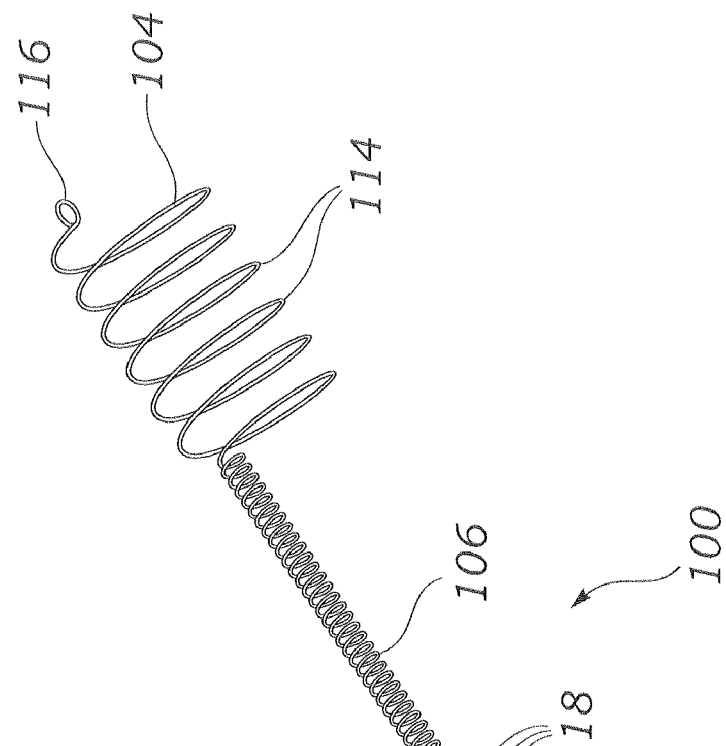
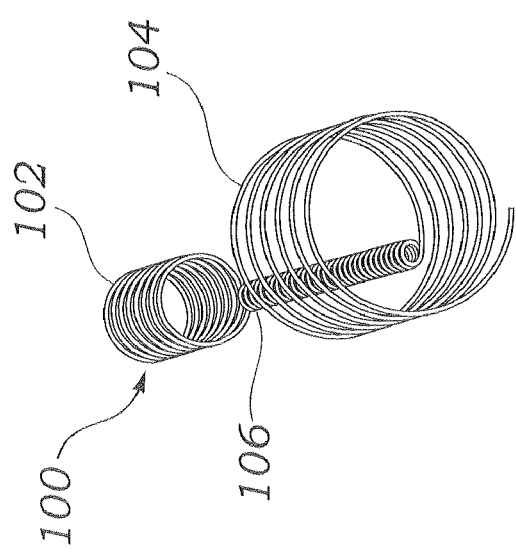
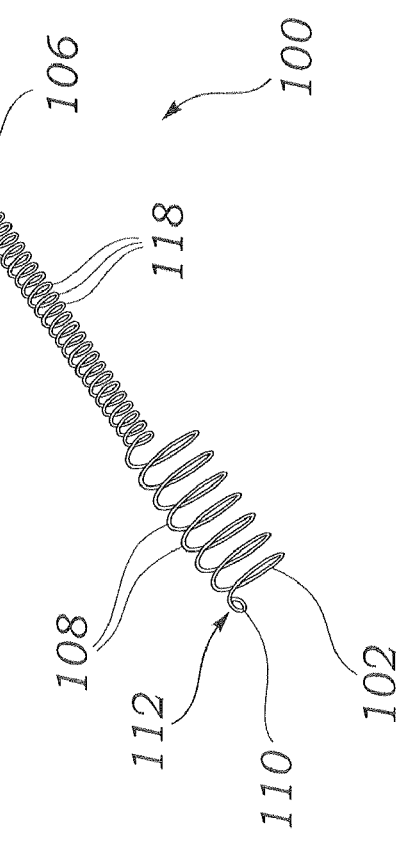

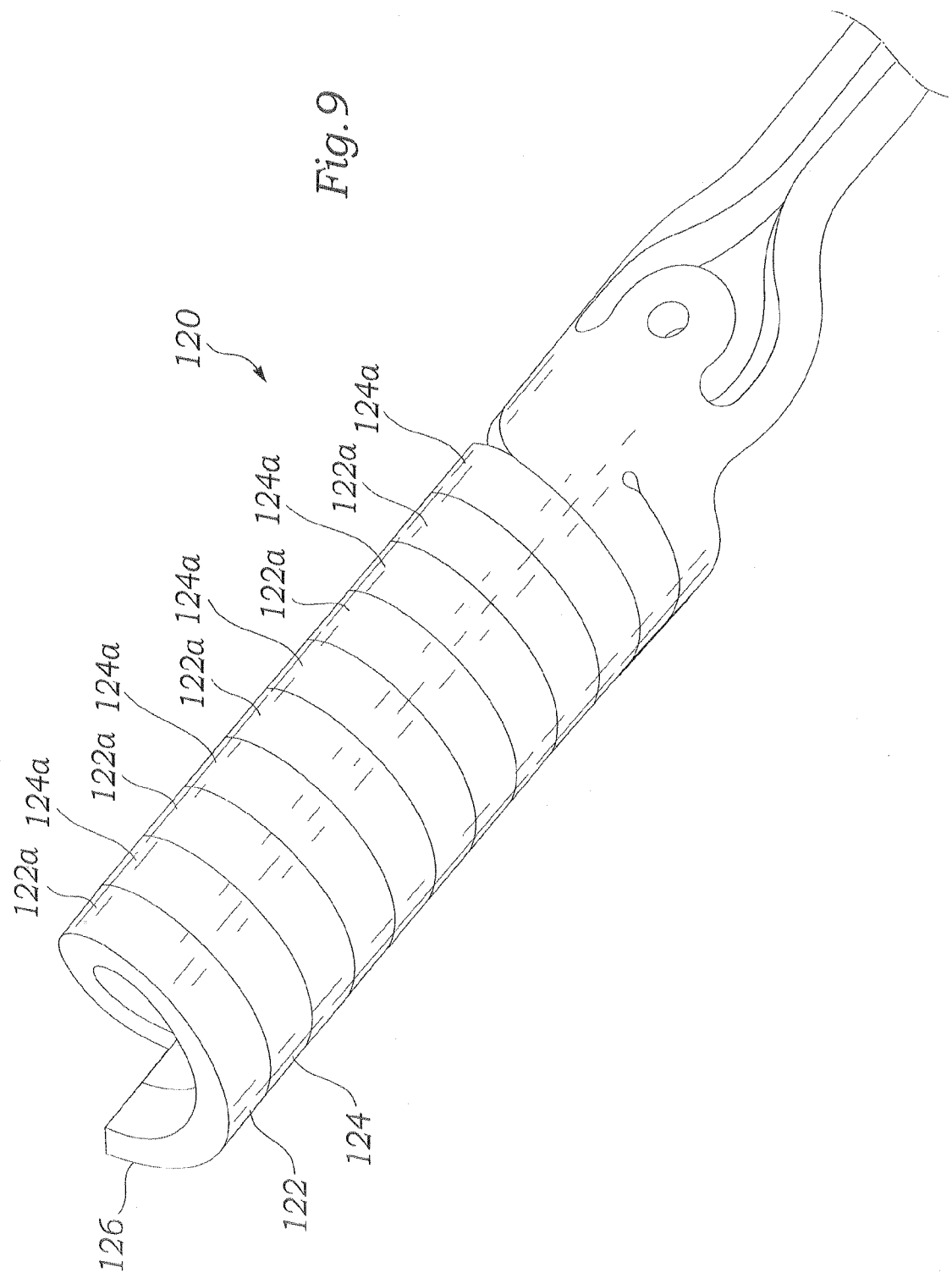

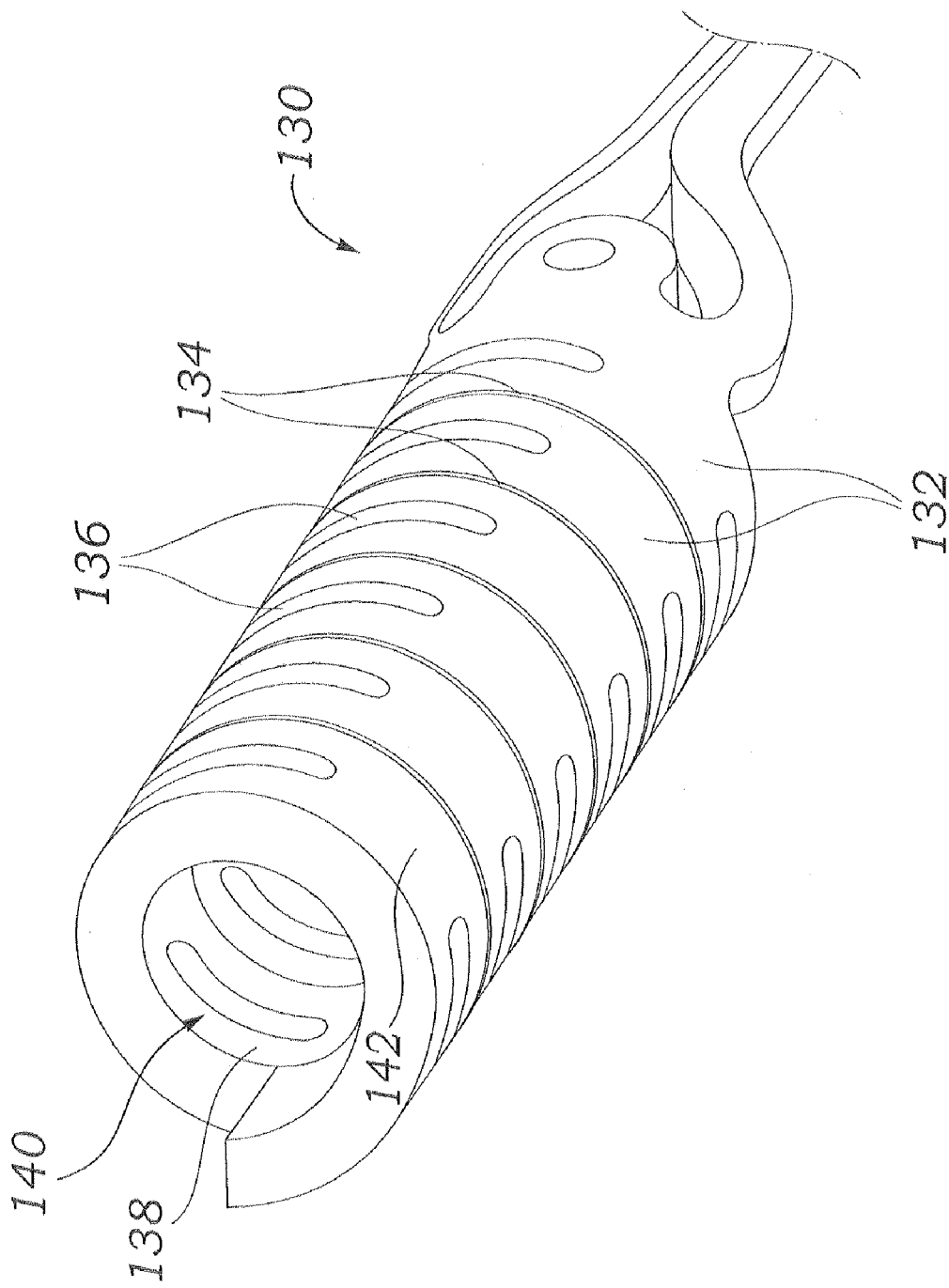

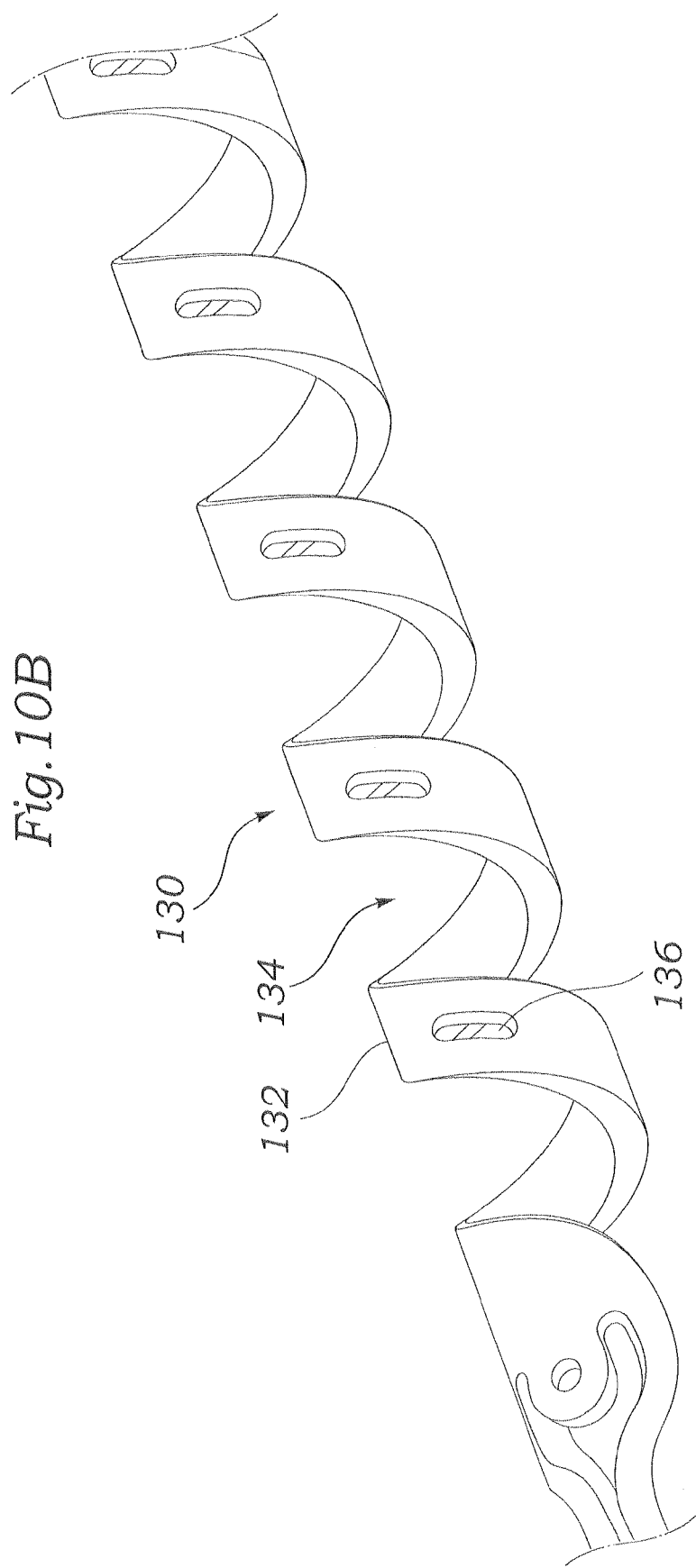

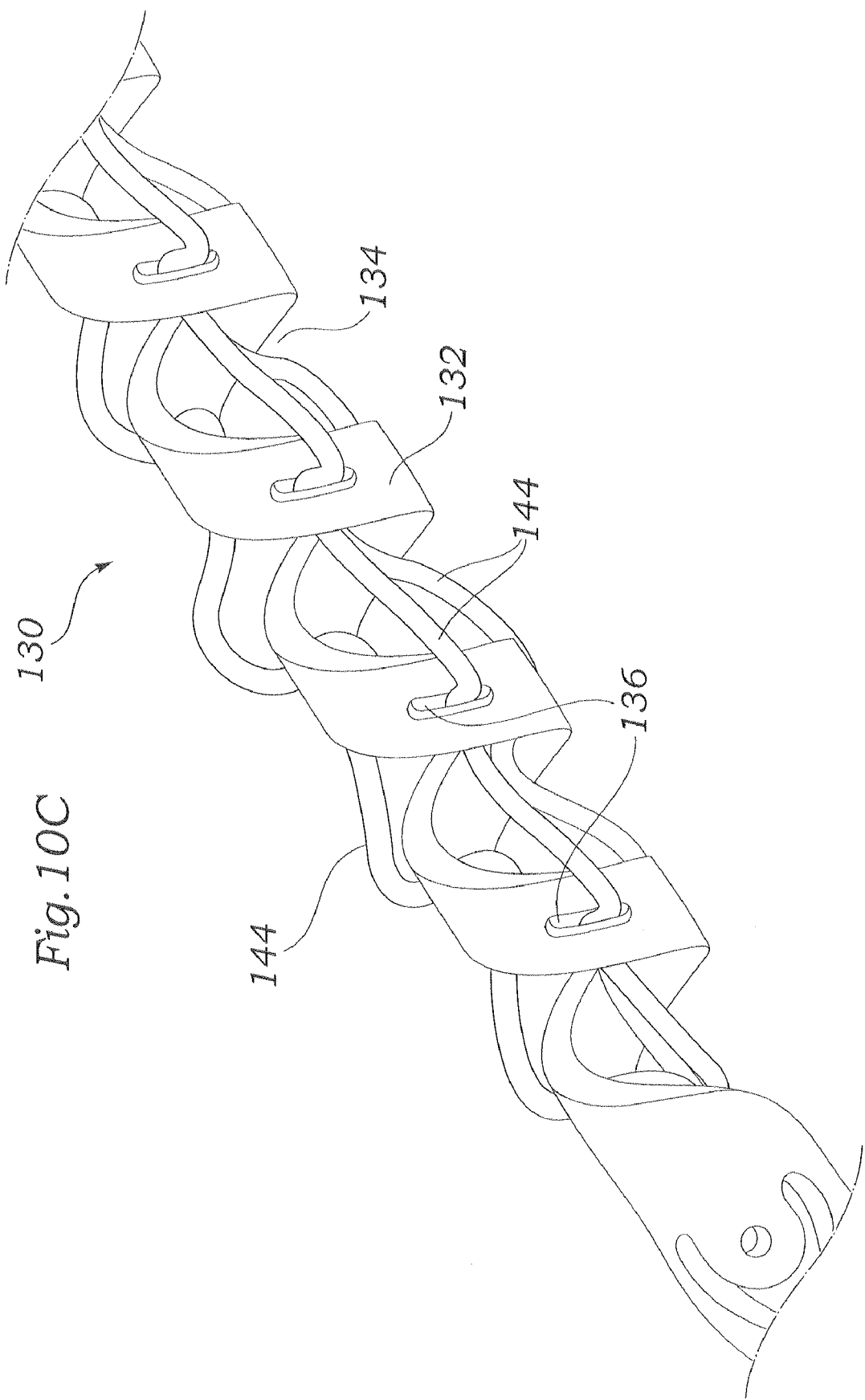

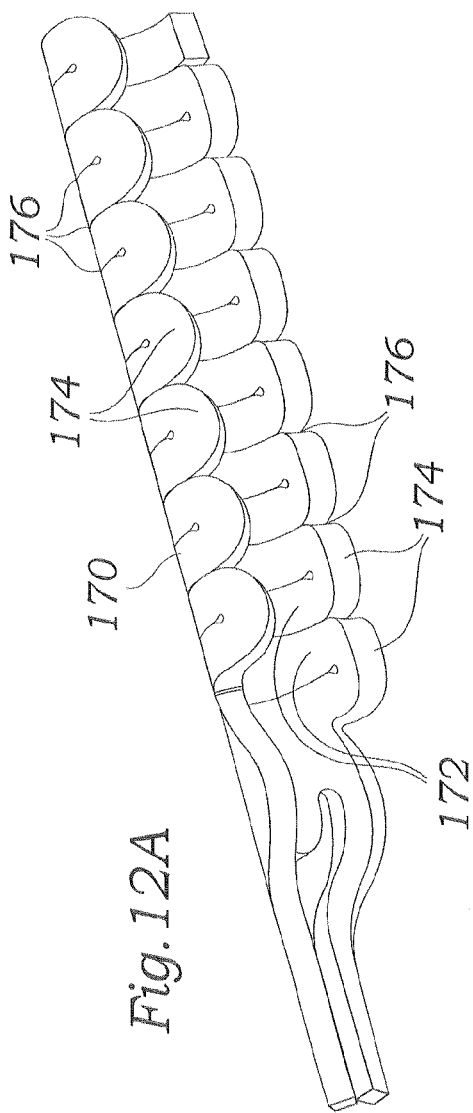
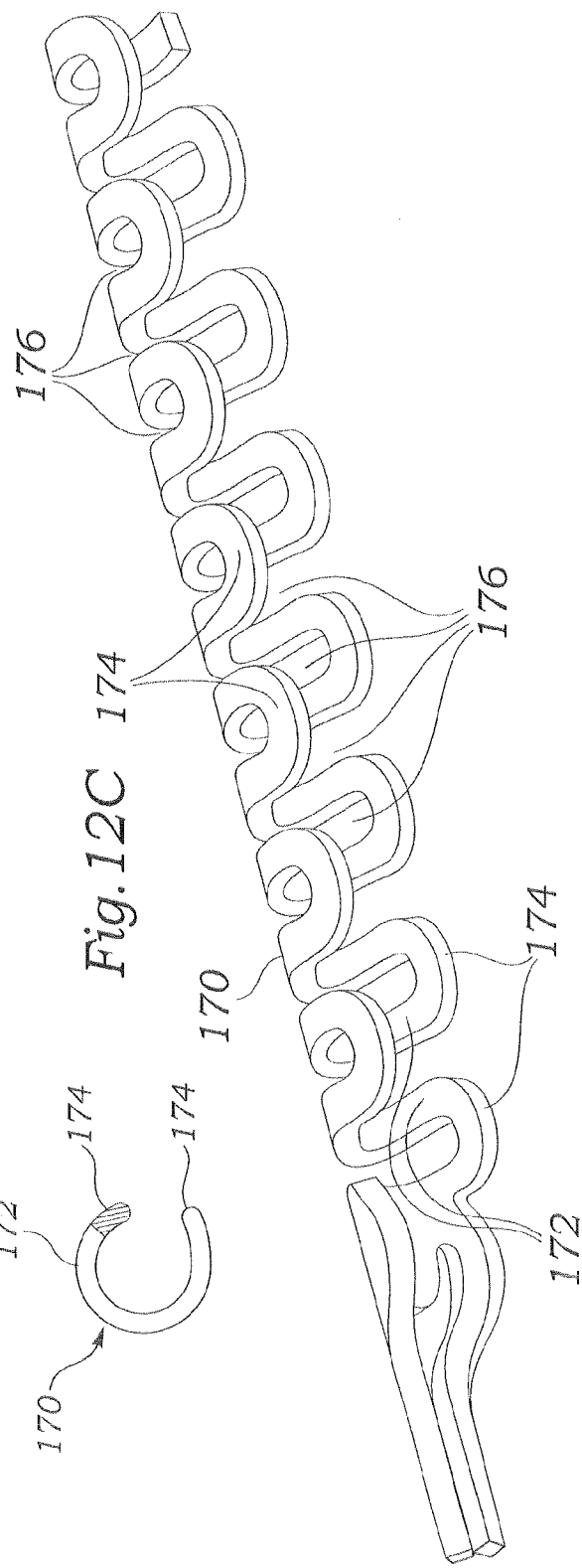
Fig.12A
Fig.12B
Fig.12C

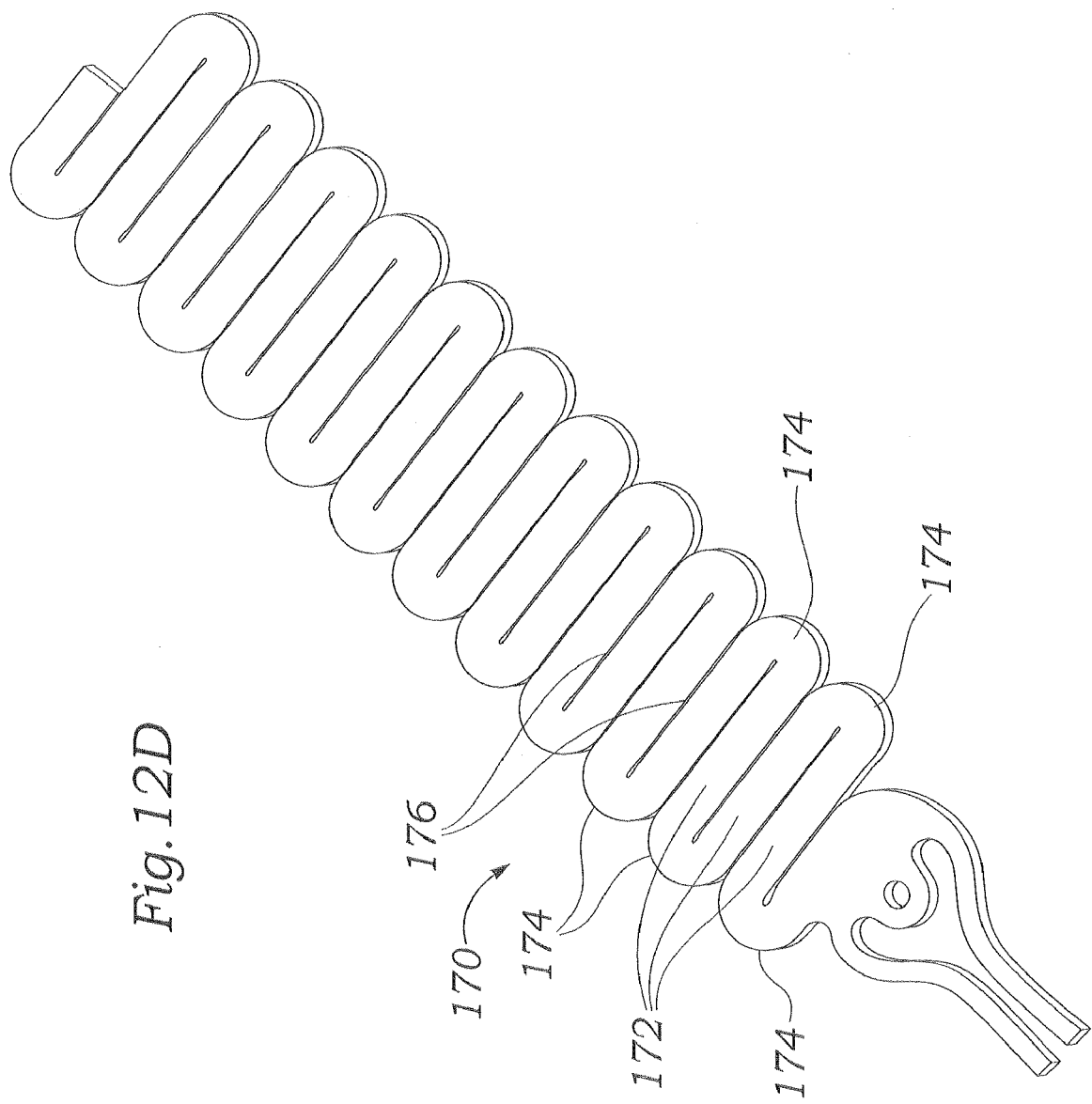

COILED IMPLANT FOR MITRAL VALVE REPAIR

CROSS REFERENCE TO RELATED APPLICATIONS

The present application claims priority to U.S. Provisional Patent Application No. 60/772,984, filed on Feb. 9, 2006, entitled "Coiled Implant for Mitral Valve Repair," the disclosure of which is incorporated by reference herein in its entirety.

FIELD OF THE INVENTION

The present invention relates to a medical implant, and more particularly to a medical implant for treating a mitral valve.

BACKGROUND

Heart valve regurgitation, or leakage from the outflow to the inflow side of a heart valve, is a condition that occurs when a heart valve fails to close properly. Regurgitation through the mitral valve is typically caused by changes in the geometric configurations of the left ventricle, papillary muscles and mitral annulus. Similarly, regurgitation through the tricuspid valve is typically caused by changes in the geometric configurations of the right ventricle, papillary muscles and tricuspid annulus. These geometric alterations result in incomplete coaptation of the valve leaflets during systole.

A variety of heart valve repair procedures have been proposed over the years for treating defective heart valves. With the use of current surgical techniques, it has been found that between 40% and 60% of regurgitant heart valves can be repaired, depending on the surgeon's experience and the anatomic conditions present. The advantages of heart valve repair over heart valve replacement are well documented. These advantages include better preservation of cardiac function and reduced risk of anticoagulant-related hemorrhage, thromboembolism and endocarditis.

In recent years, several new minimally invasive techniques have been introduced for repairing defective heart valves wherein surgery and cardiopulmonary by-pass are not required. Some of these techniques involve introducing an implant into the coronary sinus for remodeling the mitral annulus. The coronary sinus is a blood vessel that extends around a portion of the heart through the atrioventricular groove in close proximity to the posterior, lateral and medial aspects of the mitral annulus. Because of its position, the coronary sinus provides an ideal conduit for receiving an implant (i.e., endovascular device) configured to act on the mitral annulus.

As a result of the development of implants configured for insertion into the coronary sinus for repairing mitral valves, new systems and methods for delivering these implants have also been developed. For example, U.S. Pat. No. 6,210,432 to Solem et al., the entire disclosure of which is incorporated herein by reference, describes a stabilizing instrument onto which an implant may be mounted using a locking device including a pair of spring blades and knobs. After the implant is placed in a desired location in a patient, a catheter may be used to release the implant from the stabilizing instrument. In another example, U.S. Pat. No. 6,402,781 to Langberg et al. describes a deployment system including an introducer sheath and a pusher mechanism. The implant is contained within the introducer sheath during advancement into the coronary sinus. After reaching the desired location, the pusher mechanism is used to hold the implant in a fixed position while the introducer sheath is retracted. Yet another example of a delivery system is disclosed in Applicant's co-pending application Ser. No. 11/238,853, filed Sep. 28, 2005. This delivery system is configured to deliver and deploy a medical implant in a very predictable and secure manner. The delivery system is also configured for easy pre-procedure and peri-procedure flushing of all of the delivery lumens as well as adequate purging of air bubbles trapped in the catheter system to minimize the potential for air embolization during use of the delivery system.

Although a variety of implants and delivery systems have been proposed for treating mitral valve regurgitation in a minimally invasive manner, it has been found that existing implant configurations may lack the structural integrity necessary to effect a change to the mitral annulus located adjacent the coronary sinus. Accordingly, a need exists for an improved implant sized to be anchored at least partially within a coronary sinus and having sufficient strength to apply a compressive force along the mitral annulus for treating mitral valve regurgitation. It is desirable that such an implant be configured to evenly distribute forces to minimize stress concentrations and thereby reduce the possibility of fracture. It is also desirable that such an implant include anchoring portions which are capable of securely engaging an interior wall of the coronary sinus and/or coronary ostium or right atrium while being compressible for delivery to the treatment site. It is also desirable that such an implant be configured for percutaneous delivery and be relatively easy to manufacture. The present invention addresses these needs.

SUMMARY OF THE INVENTION

Various embodiments of the present invention provide devices and methods for treating mitral valve regurgitation in a minimally invasive manner. Certain embodiments are particularly well adapted for delivery at least partially into a coronary sinus for applying a compressive force along a posterior portion of the mitral annulus.

In one embodiment, an apparatus for treating a mitral valve comprises an elongate member having a spiral shape, the elongate member having a proximal end portion and a distal end portion, an expandable proximal anchor joined to the proximal end portion of the elongate member, and an expandable distal anchor joined to the distal end portion of the elongate member. The elongate member is configured to adjust from an elongated state to a shortened state after delivery at least partially into a coronary sinus for reshaping a mitral annulus. A resorbable material may be inserted between coils of the elongate member to temporarily maintain the elongate member in its elongated state. The elongate member may also contain windows in the coils of the spiral, the windows adapted to receive a resorbable thread.

In an alternate embodiment, the elongate member may have a generally sinusoidal design. In yet another alternate embodiment, the expandable proximal and distal anchors may also have a spiral shape.

The elongate member may be joined to the anchors in various ways, including via flexible suture, loops, links, and/or hinge-like mechanisms. The implant may be formed from separate elements that are joined together by, for example, welding, crimping, bolting, or suturing. The implant may be made integrally from a single piece of material, such as wire, tube, ribbon, or plate.

Additionally, a method for treating a mitral valve using an implant is provided, the method including inserting the implant at least partially into the coronary sinus, expanding and anchoring the expandable distal anchor in the coronary sinus, pulling the expandable proximal anchor in a proximal direction, expanding and anchoring the expandable proximal anchor in the coronary sinus or outside the coronary sinus (e.g., in the ostium or right atrium), and allowing the resorbable material to be resorbed, causing the bridge to shorten and thereby reshape a mitral annulus.

BRIEF DESCRIPTION OF THE DRAWINGS

FIGS. 2A, 2B, and 2C are side, cross-sectional, and cross-sectional views, respectively, of an implant in a delivery/compressed state according to an embodiment of the invention;

FIGS. 3A, 3B, and 3C are side, cross-sectional, and cross-sectional views, respectively, of the implant from FIGS. 2A, 2B, and 2C, in a deployed/expanded state according to an embodiment of the invention;

FIG. 4 is a side view of the implant of FIGS. 2A-3C in a contracted/shortened state according to the invention;

FIG. 5A is a side view of an implant according to a further embodiment of the invention;

FIG. 5B is a close-up perspective view of a bridge from the implant from FIG. 5A;

FIG. 5C is a top view of the implant of FIG. 5A;

FIGS. 8A and 8B depict perspective and side views, respectively, of an implant according to an embodiment of the invention;

FIG. 9 depicts a perspective view of a dual-coiled bridge according to an embodiment of the invention;

FIG. 10A is a perspective view of a bridge according to an embodiment of the invention;

FIG. 10B is a side view of the bridge of FIG. 10A in a lengthened/stretched state;

FIG. 10C is a side view of the bridge of FIG. 10B with resorbable material threaded through the windows thereof;

FIGS. 12A and 12B are perspective and cross-sectional views, respectively, of a bridge according to an embodiment of the invention;

FIG. 12C is a perspective view of the bridge of FIG. 12A in a lengthened/stretched state;

FIG. 12D is a perspective view of a bridge according to an embodiment of the invention.

DETAILED DESCRIPTION OF PREFERRED EMBODIMENTS

Figure 1:
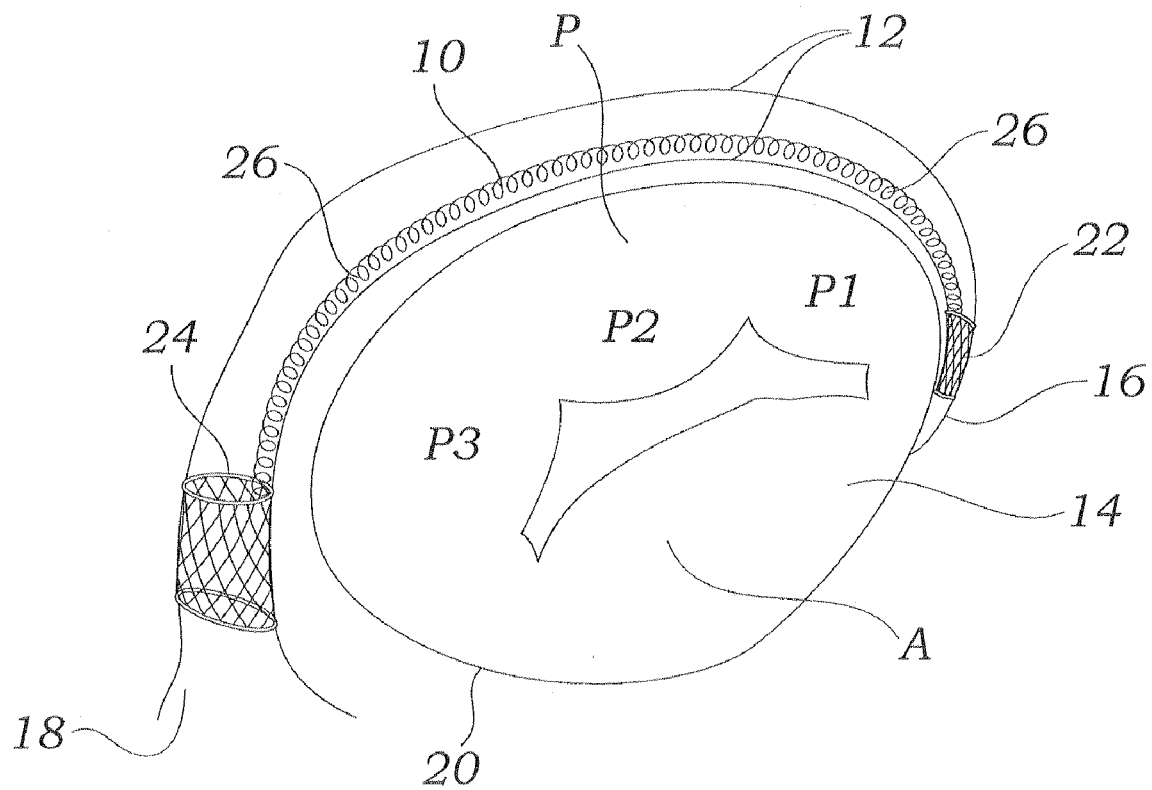
FIG. 1 is a three-dimensional view of an implant deployed in the coronary sinus according to one preferred embodiment of the present invention.

FIG. 1 depicts an implant 10 of the current invention deployed in the coronary sinus 12 of a mitral valve 14. From this view, it can be seen that the coronary sinus 12 extends around a posterior region of the mitral valve 14. The coronary sinus 12 is a relatively large vessel that receives venous drainage from the heart muscle. Blood flows through the coronary sinus 12 from a relatively narrow distal portion 16 and empties into the right atrium through a relatively wide coronary ostium 18. The mitral valve 14 generally includes an anterior leaflet A and a posterior leaflet P. The posterior leaflet P is formed with three scallops P1, P2, and P3. A mitral annulus 20 is a portion of tissue surrounding the mitral valve 14 to which the valve leaflets A, P attach. The coronary sinus 12 passes around the mitral valve 14 generally parallel to the mitral annulus 20 adjacent the posterior leaflet P.

As used herein, the term coronary sinus 12 is used as a generic term that describes the portion of the vena return system that is primarily situated adjacent to the mitral valve 14 and extends, at least in part, along the atrioventricular groove. Accordingly, the term "coronary sinus" may be construed to include the great cardiac vein and all other related portions of the vena return system.

It has been found that dilation of the mitral annulus 20 is the primary cause of regurgitation (i.e., reversal of flow) through the mitral valve 14. More particularly, when a posterior aspect (i.e., portion adjacent the posterior leaflet P) of the mitral annulus 20 dilates, one or more of the posterior leaflet scallops P1, P2, or P3 typically moves away from the anterior leaflet A. As a result, the anterior and posterior leaflets A, P fail to properly align and meet to completely close the mitral valve 14, and blood is capable of flowing backward through the resulting gap.

Reducing the dilation of the posterior aspect of the mitral annulus 20 can reduce and even eliminate mitral regurgitation. It has been found that applying tension within the coronary sinus 12 can alter the curvature of the coronary sinus 12, and thereby create a corresponding change in the dilation of the posterior aspect of the mitral annulus 20. As depicted in FIG. 1, the implant 10 applies tension within the coronary sinus 12, thereby pulling the coronary sinus 12 into a more straightened (i.e., less curved or dilated) configuration, which creates a corresponding reshaping of the posterior aspect of the mitral annulus 20. The implant 10 thus causes movement the posterior aspect of the mitral annulus 20 in an anterior direction, thereby moving the posterior leaflet P closer to the anterior leaflet A and closing the gap caused by the leaflet displacement.

The implant 10 includes a distal anchor 22, a proximal anchor 24, and a connecting bridge 26. The particular connecting bridge 26 depicted is a coiled structure extending from the distal anchor 22 to the proximal anchor 24. The distal anchor 22 is depicted deployed in a generally narrow portion of the coronary sinus 12, while the proximal anchor 24 is deployed in a somewhat wider portion of the coronary sinus 12 adjacent the coronary ostium 18. The connecting bridge 26 pulls the distal and proximal anchors 22, 24 toward each other, thereby changing the curvature of the coronary sinus 12 and moving the posterior leaflet P toward the anterior leaflet A. Note that the proximal anchor could also be deployed outside of the coronary sinus, e.g., in the ostium or right atrium.

The particular deployment locations for the distal anchor 22 and proximal anchor 24 depends on the particular application, including such factors as the condition of the mitral valve (and the desired correction thereof), the patient's particular vascular system (including the coronary sinus), etc. The distal anchor 22 can be deployed in the great cardiac vein (GCV) in a location between the left anterior descending coronary artery (LAD) and the circumflex artery (LCX). More particularly, as is known in the art, there is a triangular region formed between and generally bounded by the LAD, the LCX, and the GCV. By deploying the distal anchor in the GCV in a position within this generally triangular region, and specifically (depending on the particular application) within the portion of the region that is closely adjacent the intersection of the LAD and the LCX, the distal anchor 22 may be deployed in a secure position while possibly reducing any chance of obstructing blood flow and/or otherwise interfering with arterial performance and/or condition.

As used herein, "distal" means the direction of a device as it is being inserted into a patient's body or a point of reference closer to the leading end of the device as it is inserted into a patient's body. Similarly, as used herein "proximal" means the direction of a device as it is being removed from a patient's body or a point of reference closer to a trailing end of the device as it is inserted into a patient's body.

As illustrated in FIGS. 2A-2C, an implant 10 includes a distal anchor 22 and a proximal anchor 24 connected by a bridge 26, with the bridge 26 formed from a plurality of coils 28. A resorbable material 30 is disposed within openings 32 between coils 28 in the bridge 26. The distal anchor 22 has a length 34 and diameter 36. The proximal anchor also has a length 38 and diameter 40. The respective diameters 36, 40 of the distal and proximal anchors 22, 24 are relatively small during delivery, as depicted in the end views of the distal anchor 22 in FIG. 2B and the proximal anchor 24 in FIG. 2C, to permit the anchors 22, 24 to be advanced within a patient's vasculature to the desired deployment site, e.g., within a coronary sinus. In the particular embodiment depicted in FIGS. 2A-2C, the distal and proximal anchors 22, 24 have generally equal lengths 34, 38 as well as generally equal diameters 36, 40 during delivery. However, depending on the particular embodiment, the distal anchor could have a different length and/or diameter than the proximal anchor.

In the delivery/compressed state depicted in FIG. 2A, the bridge 26 has a length 42, which when combined with the lengths 34, 28 of the anchors 22, 24 defines the overall implant length 44.

The proximal and distal anchors 22, 24 each have a compressed state for delivery, depicted in FIGS. 2A-2C, and an expanded/deployed state, depicted in FIGS. 3A-3C. In the compressed state of FIGS. 2A-2C, the anchors 22, 24 each have diameters 36, 40 that are less than the diameter of the vessels through which the anchors are to be advanced and/or deployed, such as the coronary sinus. In one preferred embodiment, the anchors 22, 24 in a compressed/delivery state have a substantially uniform diameter of between about 1.5 mm and 4 mm.

FIGS. 3A-3C depict the implant 10 in its expanded/deployed state, where the anchors 22, 24 have been expanded so that their diameters 36, 40 are substantially larger than they were during the compressed/delivery state. In one preferred embodiment of an expanded state, depicted in FIGS. 3A-3C, the diameters 36, 40 of the respective anchors 22, 24 are about equal to or greater than a diameter of the particular section of a non-expanded coronary sinus in which each anchor will be deployed. Since the coronary sinus generally has a greater diameter at its proximal end than at its distal end (and the coronary ostium and right atrium are even larger than the proximal portion of the coronary sinus), the diameter 36 of the expanded/deployed distal anchor 22 is smaller than the diameter 40 of the expanded/deployed proximal anchor 24. In one preferred embodiment, the distal anchor diameter 36 is between about 3 mm and 8 mm when the distal anchor is deployed, and the proximal anchor diameter 40 is between about 10 mm and 18 mm when the proximal anchor is deployed. Note, however, that an implant according to the invention may have dimensions outside of the recited ranges, depending on the particular application and embodiment. For example, an implant configured to be implanted with the proximal anchor deployed in the coronary ostium may have a proximal anchor with a larger diameter than a similar implant configured to be deployed with the proximal anchor deployed well within the coronary sinus.

FIGS. 3A-3C depict the generally dimensions of the implant 10 after deployment in, for example, a coronary sinus. (The bridge 26 is depicted in FIG. 3A for reference purposes only as being generally straight: Note that after deployment the bridge 26, which is generally flexible, will generally assume a curved shape that may roughly correspond to the shape of the vessel in which it is deployed.) Note that the bridge length 42 is essentially the same between the compressed/delivery state depicted in FIG. 2A and the expanded/deployed state depicted in FIG. 3A. The overall implant length 44 is also essentially the same between the compressed/delivery state depicted in FIG. 2A and the expanded/deployed state depicted in FIG. 3A, although, depending on the particular embodiment, some foreshortening of the overall length 44 may occur as a result of any shortening that might occur to the anchors 22, 24 during expansion.

The resorbable material 30 holds the bridge 26 in an elongated state during delivery and deployment, as depicted in FIGS. 2A and 3A. However, over time, the resorbable material 30 is resorbed such that the coils 28 will move together to close the openings 32 therebetween, thus causing the bridge 26 to shorten, as depicted in FIG. 4. The shortening of the bridge length 42 causes the bridge 26 to pull on the anchors 22, 24, causing the implant 10 to be reshaped and thereby causing a corresponding reshaping of the coronary sinus and heart valve annulus.

Resorbable materials are those that, when implanted into a human body, are resorbed by the body by means of enzymatic and/or hydrolytic degradation and/or by active absorption by blood cells and tissue cells of the human body. Examples of such resorbable materials include resorbable metals, such as magnesium alloys and zinc alloys, and resorbable polymers such as PDS (Polydioxanon), Pronova (Poly-hexafluoropropylen-VDF), Maxon (Polyglyconat), Dexon (polyglycolic acid), and Vicryl (Polyglactin).

The rate at which the bioresorbable material is resorbed (and, accordingly, the rate at which the bridge shortens) can be varied by selecting materials that are resorbed faster and/or slower, depending on the particular application. For example, an implant whose bridge structure includes bioresorbable materials that are resorbed relatively quickly will have a bridge that shortens relatively quickly, while the use of slower-resorbing materials will cause the bridge to shorten at a slower rate. Additionally, the bioresorbable material might be selected to have different resorb rates at different positions along the length of the bridge. For example, the bioresorbable material located near the center portion of the bridge might be selected to resorb more quickly than the bioresorbable material that is closer to one or both of the anchors, thereby providing an implant that will shorten in the middle portion of the bridge before shortening in one or both end portions. Other embodiments are also within the scope of the invention, including using materials to cause one or more end portions to shorten more quickly than the center portion and/or an opposing end portion of the bridge.

Bioresorbable materials can be irradiated to provide different resorbing rates. By treating bioresorbable materials with radiation, the resorbable rate of the particular materials can be altered. By using different radiation dosages and/or different radiation sources (e.g., x-rays or gamma rays, etc.) to treat the bioresorbable material (e.g., bioresorbable suture), the resorbable rate of the particular materials can be selectively altered in order to achieve the desired rate by which the shape and/or other configuration of the implant is altered. For example, radiation could be selectively applied to the bioresorbable material 30 used in the bridge 26 depicted in FIGS. 2-4, thereby providing a desired rate by which the bioresorbable material is resorbed and also providing a desired rate by which the bridge 26 will shorten. The application of radiation (to alter the resorb rate) can be performed during construction of the device, just prior to deployment, or even within the patient's body (during and/or after deployment). Moreover, the application of radiation can be varied along the length of the bridge (and along the length of the bioresorbable material) to provide different bioresorbable rates (and hence different shortening rates) at different portions along the length of the bridge.

Bioresorbable material may be used in combination with a shape memory material, such as Nitinol, Elgiloy, or spring steel, to allow the superelastic material to return to a predetermined shape over a period of time. In the particular embodiment shown in FIGS. 2A-4, the proximal and distal anchors 22, 24 are both generally cylindrical and are made from tubes of shape memory material, such as, for example, Nitinol. However, the anchors 22, 24 may be made from any suitable material, such as stainless steel. In the illustrated embodiment, both anchors 22, 24 have a mesh configuration. Although one particular type of anchor mechanism and structure is shown for purposes of illustrating this particular embodiment, it will be appreciated that a variety of alternative anchoring mechanisms may be used.

FIGS. 5A-5C depict a medical implant 60 having a distal anchor 62, a proximal anchor 64, and a bridge 66 extending between the distal and proximal anchors 62, 64. In the illustrated configuration, the bridge 66 is an elongate member formed with a generally spiral configuration, similar to a coil spring. Note that no bioresorbable material is present in the particular embodiment of FIGS. 5A-5C, although such material could be included in accordance with the invention. In the preferred embodiment depicted in FIGS. 5A-5S, the bridge 66 includes at least twenty coils 68, with gaps or spaces 70 disposed between adjacent coils 68. Note that other numbers of coils (i.e., fewer coils or more coils) are also within the scope of the invention, with the number of coils depending on the particular application and embodiment. For example, a bridge could be formed from approximate fifty (50) coils, with each coil having a length of about 1 mm with spaces disposed therebetween. (Note that in FIG. 5C the bridge 66 is depicted in its completed cylindrical shape, while the anchors 62, 64 are depicted in a flattened, unrolled condition that might occur during manufacture, such as where the anchors are formed by cutting a flat sheet and then rolling the sheet into a cylindrical shape.)

Links 72, 74 join the distal and proximal anchors 62, 64, respectively, to the coils 68 of the bridge 66. The bridge 66 may be manufactured from any suitable material, such as, for example, Nitinol, Elgiloy, Cobalt-Chromium, other super alloys, or stainless steel. The spiral configuration is well suited for allowing the bridge to be stretched along a longitudinal axis. The spiral configuration can also provide the bridge 66 with a lumen configured to receive a guidewire, thereby facilitating advancement of the implant to a treatment site.

In one preferred method of manufacture, the bridge may be laser-cut from a tube, or laser-cut from a flat sheet that is then rolled or otherwise formed into a generally tubular structure. In another preferred method of manufacture, the bridge may be formed or shape-set into a spiral configuration.

The bridge 66 may be joined to the anchors 62, 64 in a variety of ways. In the particular embodiment of FIGS. 5A-5C, links 72, 74 join the distal and proximal anchors 62, 64, respectively, to the bridge 66. The links 72, 74 each have a base 76 and arms 78 that extend from the base 76, with the arms 78 being connected to the anchors 62, 64. Further, one or both of the links 72, 74 may be provided with a hole 80 which serves to secure a resorbable thread, as will be described in more detail below. Alternatively, the anchors 62, 64 may be joined directly to the bridge 66 (i.e., without links), as will be described below in more detail. In other embodiments the bridge is joined to one or more anchors via flexible suture, loops, or a hinge-like mechanism.

The spiral configuration of the bridge 66 is capable of providing an additional degree of movement in which the bridge can generally freely move, and in particular allows the implant 60 to be twisted along its longitudinal axis without producing substantial stresses on the structure of the bridge 66 or other implant structures. Therefore, the implant 60 may be delivered with the distal and proximal anchors 62, 64 in any desired rotational alignment without substantially affecting the structural integrity of the implant 60. This is a particularly advantageous feature because the coronary sinus generally extends along a three-dimensional path, and therefore it may be desirable to deploy the distal and proximal anchors 62, 64 at different rotational alignments relative to the bridge 66. Furthermore, allowing an adjustable rotational alignment of the anchors 62, 64 and the bridge 66 minimizes the tensile strain at the interface (e.g., the links 72, 74) between the anchors 62, 64 and the bridge 66, thereby lessening the stiffness discrepancy between the bridge 66 and the interface and more evenly distributing the stress throughout the implant 60. Thus, the implant 60 can maintain structural integrity even when it is subjected to relatively high stresses in the coronary sinus.

The bridge 66 is configured to stretch longitudinally such that the bridge 66 has an elongated state and a shortened state. In one preferred embodiment, the bridge 66 is biased to be in the shortened (i.e., relaxed) state, in which the bridge 66 may have a length of between about 40 to 54 mm. In one embodiment of the invention, the bridge 66 in the elongated state may be stretched to a length between about 150% and 200% of its relaxed length. Note that other lengths and elongated-to-relaxed-length ratios are also within the scope of the invention, depending on the particular application and embodiment. The bridge 66 may be delivered entirely or partially into the coronary sinus in the elongated state, for example, using a delivery system of the type described in U.S. patent application Ser. No. 11/238,853, the entire contents of which are expressly incorporated herein by reference.

In one embodiment, an implant according to the invention may be used to acutely alter the shape of the mitral annulus. In this method, the distal anchor is deployed and secured in the coronary sinus. The proximal anchor is then pulled from a location outside the body to acutely reshape the mitral annulus. The pulling force may also cause the bridge itself to elongate. The proximal anchor is then deployed in the coronary sinus or outside the coronary sinus (e.g., in the coronary ostium or right atrium) to maintain the mitral annulus in the reshaped condition.

Because the bridge is in the elongated state (and may have been additionally stretched during the "pulling" discussed above), tension in the bridge may pull on the distal and proximal anchors to further reshape the mitral annulus even after both anchors have been deployed.

In one configuration, the delivery system maintains the bridge in the elongated state during delivery and anchors the implant at least partially within the coronary sinus while in the elongated state such that the tension in the bridge affects the geometry of the mitral annulus. In another configuration, the delivery system is used to stretch the bridge into the elongated stated during the delivery process. More particularly, the bridge is stretched by pulling on the proximal anchor after the distal anchor has been deployed in the coronary sinus. After creating sufficient tension in the bridge, the proximal anchor is then deployed for holding the bridge in the elongated state.

Due to the shape and location of the coronary sinus, the tension in the bridge pulls inward along an inner wall of the coronary sinus for applying an inward force along a posterior aspect of the mitral annulus. The force pulls the posterior leaflet of the mitral valve toward the anterior leaflet, thereby reducing mitral valve dilatation and improving leaflet coaption. As noted above, an implant formed with a spiral bridge may provide greater flexibility during delivery. Furthermore, it will be recognized that an implant formed with a spiral bridge may provide other advantages. For example, an implant having a stretchable (e.g., spiral) bridge portion may change length as the heart moves during each beat, thereby relieving stress on the coronary sinus and allowing the heart to function in a more natural manner. Additionally, the spiral bridge substantially maintains its original structure and length after being cyclically stretched and relaxed by the beating heart. Because the movements are within the elastic range of the material, the bridge exhibits little or no plastic deformation over time.

In another advantageous feature, it will be recognized that the coiled construction of the bridge distributes stresses more evenly throughout the implant. As discussed above, the bridge may be stretched into an elongated state before or during implantation. Furthermore, during implantation, the implant is typically bent and twisted to conform to the shape of the coronary sinus. The spiral shape of the bridge advantageously allows the longitudinal, bending and torsional forces to be distributed evenly along the bridge. This is particularly advantageous for reducing stress concentrations and thereby enhancing the structural integrity of the implant. It has also been found that the spiral bridge allows the implant to be stretched substantially (e.g., 200%) while remaining within the elastic range of the material used to form the bridge. In some preferred embodiments, an implant having a spiral bridge remains within the elastic region even after having been stretched to 200% of its length or greater. Because of its ability to be stretched to twice its relaxed length without reducing the structural integrity of the implant, a relatively short bridge may be used to achieve the same cinching effect as bridges having other structural configurations. In addition, it will be recognized that a spiral bridge of the same length as bridges having other structural configurations can achieve greater cinching. Other properties of the bridge may also be adjusted. For example, additional coil windings lower the spring constant of the bridge to make the bridge less stiff. Further, larger diameter spring coils also lower the spring constant and increase bending stiffness.

The embodiment of an implant shown in FIGS. 5A-5C is configured to acutely affect the mitral annulus. However, as discussed above with respect to FIGS. 2-4, the implant may also be configured (e.g., through the use of bioresorbable and/or memory materials) to delay and/or reduce the rate at which the bridge shortens after implantation. In one advantageous feature, delayed shortening ensures secure anchoring of the implant in the coronary sinus or other regions by allowing more time for tissue in-growth into the proximal and distal anchors before tension is applied to the bridge. Delayed shortening also allows the mitral annulus to be reshaped in a more gradual manner, which may be beneficial to the function of the mitral valve. To provide delayed shortening, a resorbable material such as a bioabsorbable thread is included along the bridge to temporarily maintain the bridge in the elongated state.

Figure 6:
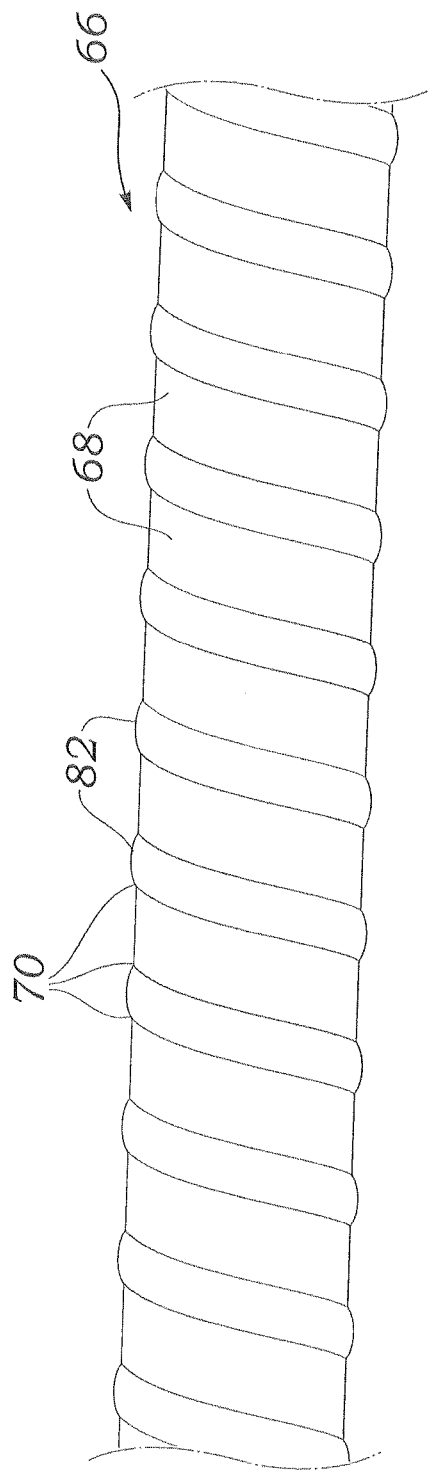
FIG. 6 depicts a close-up side view of a portion of bridge according to an embodiment of the invention.

With reference now to FIG. 6, in a variation of the embodiment described above with respect to FIGS. 5A-5C, a resorbable material 82 is provided within the spaces 70 between the coils 78 to prevent the bridge 66 from shortening. As a result, the bridge 66 is maintained in an elongated (i.e., stretched) state until the resorbable material is resorbed by the body. If desired, a portion of the resorbable material (which may be in the form of a resorbable suture) may be tied around the hole (element 80 from FIGS. 5B, 5C) in the links between the bridge 66 and a distal and/or proximal anchor to secure the resorbable material to the implant.

In one preferred method of applying the resorbable material to a spiral bridge, such as the spiral bridge 66 depicted in FIG. 6, a mandrel is inserted through a central lumen of the spiral bridge. While the bridge is held in a stretched state (thereby creating and/or enlarging the spaces between adjacent coils), a resorbable thread is spirally wrapped around the mandrel to fill the spaces between adjacent coils of the bridge. After the resorbable thread is disposed within the gaps, a shrink tubing may be applied over the bridge and a heat treatment applied to mold the thread into the gaps of the bridge. The shrink tubing and mandrel are then removed before use. In alternate methods, the resorbable material may be applied, for example, by compression molding, spray coating, or insert molding as is known in the art.

During use, the implant 60 of FIG. 6 may be deployed in a manner similar to that described above wherein the distal anchor 62 is deployed and the proximal anchor 64 is then pulled to remove slack and to achieve some reshaping of the mitral annulus, The proximal anchor 64 is deployed (either within or outside the coronary sinus) after the desired degree of reshaping has been achieved. Over time, the resorbable material 82 (e.g., resorbable suture) between the bridge coils 68 is resorbed such that the bridge 66 gradually shortens, thereby further reshaping the mitral annulus and improving mitral valve function. Alternatively, the implant 60 may be delivered entirely or partially into the coronary sinus without pulling the proximal anchor 64 during delivery. In this method, the reshaping is achieved entirely by the shortening of the bridge 66 over time.

Figure 7:
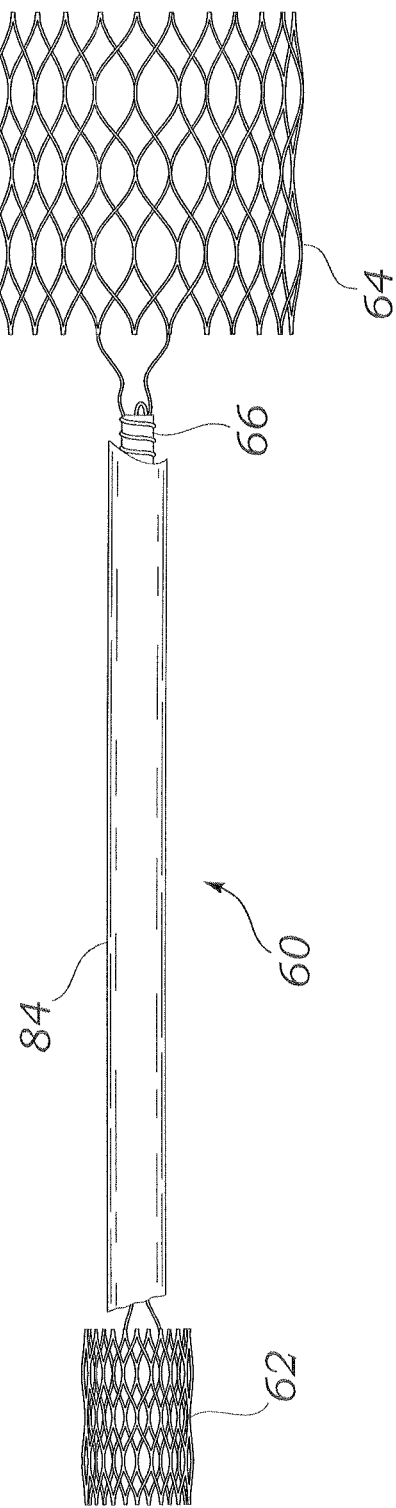
FIG. 7 depicts a side view of an implant having an outer sleeve according to an embodiment of the invention.

With reference now to FIG. 7, in another variation a sleeve 84 may be placed around the bridge 66 after the resorbable thread (or other resorbable material) has been applied. The sleeve 84 may be configured to ensure that the thread does not become dislodged from the bridge 66. Alternatively, or in addition, the sleeve 84 may provide a protective barrier to reduce the likelihood of tissue becoming pinched between the coils of the bridge 66 during shortening. The sleeve 84 may be formed of any suitable material, such as, for example, PolyTetraFluoroEthylene (PTFE). The bridge 66 may be slidable within the sleeve 84, depending on the particular embodiment. The sleeve 84 may be configured to be removed from the implant 60 prior to or during implantation, or the sleeve 84 may be configured to be implanted into the patient's body as part of the implant.

In another alternative embodiment, the sleeve 84 may be formed of a resorbable material that is resorbed by the patient's body. After the implant 60 has been inserted entirely or partially into the coronary sinus, the resorbable sleeve 84 is dissolved by the body over time, as also occurs to the resorbable material between the coils of the bridge 66 as the bridge 66 is gradually transferred from the elongated state to the relaxed state to thereby reshape the mitral annulus.

In a further embodiment, the sleeve 84 and the resorbable material between the coils of the bridge 66 can be formed as a single structure, which can be achieved by holding a bridge 66 in the elongated condition and dipping the bridge 66 into, coating the bridge 66 with, or otherwise enveloping the bridge 66 in, a resorbable material that forms both the sleeve 84 and also the resorbable structure (e.g., element 82 in FIG. 5) within the open gaps between the coils of the elongated bridge 66. In a further embodiment, a protective sleeve similar to that depicted in FIG. 7 can be used in a bridge that does not have any resorbable material between gaps or other open structures therein.

FIGS. 8A and 8B illustrate another preferred embodiment of an implant 100 according the invention. In this embodiment, the implant 100 includes a distal anchor 102, a proximal anchor 104, and a bridge 106, wherein each section (i.e., the anchors 102, 104 as well as the bridge 106) is formed with a spiral configuration similar to a coil spring. The coil shape of the anchors 102, 104 may create a tapered or straight cylindrical anchor which provides reliable traction against slippage when the implant 100 is inserted entirely or partially into the coronary sinus. In one embodiment, for ease of manufacture the implant 100 may be formed from a single wire.

In the example shown in FIG. 8B, the distal anchor 102 has a plurality of coils 108 (and in the particular embodiment depicted there are seven coils when expanded), and includes a distal eyelet 110 which may be used to hold a radiopaque marker 112 or other visualization aid. The radiopaque marker 112 on the distal eyelet 110, visible under fluoroscopy, allows the location of the distal eyelet 110 to be determined during the delivery and placement of the implant 100.

The proximal anchor 104 also has a plurality of coils 114 (and in the embodiment depicted includes six coils when expanded), and a proximal eyelet 116 that can serve as an attachment point for a retrieval mechanism in the event that the implant 100 is not deployed at the desired location or if the implant must be otherwise removed. In one example, a thread or other elongate member may extend from a location outside the patient's body through the proximal eyelet 116 and back out of the patient's body. The ends of the thread may be pulled proximally to withdraw the implant 100 from the patient's body in the event that the user desires to remove the implant 100. After the implant 100 is deployed in the desired location to the satisfaction of a user, one end of the thread may be released and the entire thread can pulled out of the proximal eyelet 116 to disengage the thread from the implant and also to pull the thread entirely out of the patient's body. Additionally, a radiopaque marker (not shown) or other visualization device may be placed in the proximal eyelet 116 which will allow the location of the proximal eyelet 116 to be identified under fluoroscopy.

The distal anchor 102 and the proximal anchor 104 each have two states: a compressed state and an expanded state. In the compressed state, the anchors 102, 104 have a diameter that is less than the diameter of the coronary sinus or other area (e.g., coronary ostium, right atrium) where they are to be advanced and/or deployed. More specifically, in an embodiment of the compressed state, the anchors 102, 104 have a substantially uniform diameter of between about 1.5 mm and 4 mm. In an embodiment of the expanded state (depicted in FIGS. 8A and 8B), the anchors 102, 104 have a diameter that is about equal to or greater than a diameter of the section of a non-expanded coronary sinus (or, for the proximal anchor, the coronary ostium or right atrium) to which each anchor 102, 104 will be aligned. Since the coronary sinus has a greater diameter at its proximal end than at its distal end (and the coronary ostium and right atrium are even larger), in one preferred embodiment of the expanded state the diameter of the proximal anchor 102 is between about 10 mm and 18 mm and the diameter of the distal anchor 324 is between about 6 mm and 8 mm.

The bridge 106 of FIGS. 8A and 8B is also formed of a plurality of coils 118, thus allowing the bridge 106 to lengthen and shorten longitudinally as well as additional freedoms of movement and rotation.

The implant 100 may be capable of collapsing into a very small cross-sectional profile during delivery. More particularly, the implant 100 may be stretched such that the implant 100 assumes a generally straightened shape for containment within a lumen of a delivery catheter. After reaching the treatment site, the implant 100 is advanced or otherwise released from the lumen and assumes its expanded spiral shape. If it is desirable to remove the implant 100, the implant 100 may be pulled back or otherwise retracted into the lumen so that the implant 100 once again is held in a straightened and stretched condition.

As discussed previously, a bridge according to the invention may be configured to shorten gradually over time. This may be achieved using a resorbable material as a spacer between coils of the bridge, as described above. When the implant is inserted into a patient, the resorbable material slowly dissolves or is otherwise absorbed by the patient's body, allowing the bridge to gradually return to the relaxed (shortened) state. In another embodiment, the bridge may be maintained in an elongated state by mechanical means, for example, by a retractable mandrel removably attached to the bridge. The retractable mandrel or other mechanical means allows for immediate, rather than delayed, cinching of the implant. Thus, when the mechanical means are used, the implant acutely cinches the coronary sinus. Note that an embodiment of the invention could combine gradual cinching with acute cinching, which could be achieved by combining resorbable material with the mechanical means. In such an embodiment, the mechanical means could provide for immediate cinching during deployment of the implant, while the resorbable material could provide for additional cinching over time.

An implant according to the invention may be made integrally from a single piece of material, such as a wire, tube, ribbon, or plate, or may be made in separate parts and joined together by, for example, welding, crimping, bolting, or suturing. The material used for the implant may include Nitinol, Elgiloy, Cobalt-Chromium, or other super alloy materials. In one exemplary embodiment, the implant may be fashioned by a process such as shape-setting, microblasting, or electro-polishing. Electro-polishing allows elimination of a passive oxide layer sometimes formed during the laser cutting process.

With reference now to FIG. 9 (which depicts a portion of a bridge 120), in yet another preferred embodiment the bridge 120 may be configured as a spiral structure including two parallel spirals 122, 124. More specifically, the bridge 120 has a similar structure to the bridge (106) from FIGS. 8A and 8B, except that rather than having a single spiral, the bridge includes two parallel spirals 122, 124 forming multiple coils 122a, 124a (where coils 122a are formed by spiral 122, and coils 124a are formed by coil 124). There are multiple spaces 126 between the coils 122a, 124a). In one preferred construction, the width of the coils 122a, 124a is about 0.5 mm. Providing narrower coils allows a greater number of coils per unit length, and thus allows a greater number of spaces per unit length. As was described above with respect to FIGS. 5A-7, resorbable material may be used in the spaces 126 between the coils 122a, 124a to maintain the bridge 120 in an elongated state and to allow for contraction of the bridge 120 over time. Since there are a greater number of spaces 126 per unit length (due to the increase number of coils 122a, 124a), the width of the spaces 126 will be smaller when the bridge 120 is stretched as compared to a single-spiral bridge having wider coils. Thus, less resorbable material is used in each space 126 between the coils 122a, 124a, allowing for faster resorption of the resorbable material and faster contraction of the bridge 120. Having two parallel coils 122, 124 also can increase the structural integrity of the bridge 120. For example, in the event that one of the coils 122, 124 fractures or is otherwise compromised, the remaining intact coil can still function to provide foreshortening, etc. to the bridge 120. Additionally, the increased number of coils 122a, 124a per unit length can provide the bridge 120 with greater flexibility, allowing the bridge 120 to conform to the tortuous anatomy of the coronary sinus. The bridge 120 may be attached to a proximal and distal anchor by any of the methods described above, for example, a link, a suture, a loop, or directly by welding.

Yet another embodiment of the invention is shown in FIGS. 10A-10C, wherein a bridge 130 is provided having a single spiral forming coils 132 and spaces 134 between adjacent coils 132. Additionally, the coils 132 have windows 136 providing an opening from an interior surface 138 (within the internal lumen 140) of the bridge 130 to an exterior surface 142 of the bridge 130. In the particular embodiment depicted in FIGS. 10A-10B, each coil 132 has three windows 136, but the present invention is not limited thereto. When in an elongated state such as the embodiment depicted in FIG. 10B, the coils 132 of the bridge 130 are stretched or otherwise positioned apart so that the spaces 134 therebetween are expanded.

As shown in FIG. 10C, a thread 144 made from, for example, bioresorbable material may be threaded through the windows 136 so as to act as a spacer between the coils 132. As shown in FIG. 10D, the thread 144 is weaved through adjacent windows 136 such that the thread 144 becomes lodged in the spaces 134 between adjacent coils 132 to thereby keep the coils 132 spaced apart and to thereby keep the bridge 130 in the elongated state. Once the implant is delivered into a patient's body, the strands of thread 144, of formed from resorbable or similar material, will dissolve over time, allowing the bridge 130 to cinch into its relaxed state. One strand of thread may be threaded through each of the three windows 136 on a coil 132 (i.e., a total of three strands are used), as depicted in the example of FIG. 10D. Threading one strand of thread 144 through each of the window 136, with each thread passing through longitudinally-adjacent windows 132 as shown, can increase the likelihood that when the thread 144 is resorbed, the bridge 130 will remain straight as it transforms into its relaxed state as opposed to becoming arched or otherwise nonuniformly cinched. However, the bridge 130 may also be used with only one or two strands of thread 144, such as where uniform cinching is not required or desired. Alternatively, the bridge 130 may also have four or more strands of thread 144, so that some of the individual windows 136 may have two or more threads 144 passing therethrough.

Figure 11:
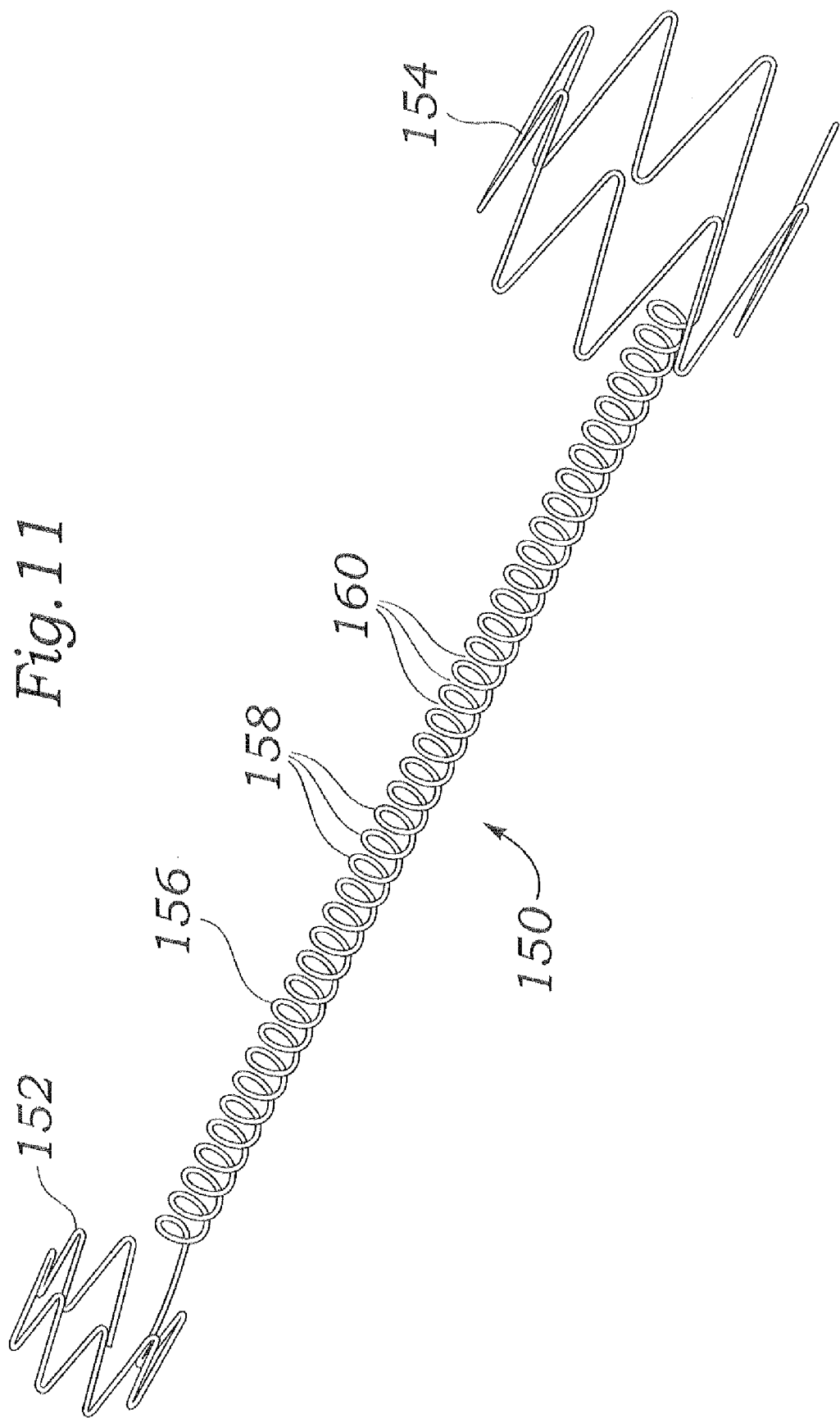
FIG. 11 is a perspective view of an implant according to an embodiment of the invention.

FIG. 11 depicts an implant 150 made from a single piece of material, for example, a nitinol wire. Such a single-piece construction can simplify the manufacturing process, reducing the time and cost of manufacturing the implant 150. The implant 150 includes a distal anchor 152 and a proximal anchor 154, with the anchors 152, 154 connected by a spiral bridge 156. The proximal and distal anchors 152, 154 each have a zig-zag structure and are substantially cylindrically shaped. However, the shapes of the anchors of the invention are not limited to these specific shapes, but can instead be of any suitable shape as is known in the art.

The spiral bridge 156 includes coils 158 separated by spaces 160. As with previously described embodiments, the spiral bridge 156 may be stretched into an elongated state and may be maintained in the elongated state by inserting resorbable material (not shown) into the spaces 160.

Because the implant 150 is made from a single piece of material (e.g., a single wire), the distal anchor 152 and proximal anchor 154 are each directly connected to the bridge 156. In one embodiment, the anchors 152, 154 have a compressed state in which the diameter of the anchor is about 2 mm, and an expanded state in which the diameter of the distal anchor 152 is about 6 to 8 mm, and the diameter of the proximal anchor is about 10 to 18 mm. In a preferred embodiment when the implant 150 is made from nitinol, the anchors 152, 154 are self-expandable from the compressed state to the expanded state.

FIGS. 12A-12D depict yet another preferred embodiment of a bridge 170 for use with an implant according to the present invention. The bridge 170 in FIGS. 12A-12B is formed to have an undulating shape (which depending on the particular embodiment may be a generally sinusoidal, zig-zag, and/or wave shape), as opposed to the spiral shape of the embodiments of FIGS. 8 and 9. FIG. 12A depicts a particular embodiment of an undulating bridge 170 after it has been fully formed, wherein the bridge 170 is formed from an undulating pattern of generally parallel elements 172, wherein adjacent parallel elements 172 are connected to each other at alternating ends by generally U-shaped connections 174. The generally parallel elements 172 and U-shaped connections define the bridge as a "partial" or "open" tubular structure, forming a generally "C"-shaped tube-like structure (as opposed to a closed "O"-shaped tube structure) in cross-section as in FIG. 12B. In one advantageous feature, the bridge 170 thus requires less material than a bridge having a "closed" or "O"-shaped tubular cross-section of the same length. The connections 174 of the bridge 170 may be rounded so as to reduce the likelihood that the bridge 170 will damage tissue.

When the bridge 170 is stretched or otherwise lengthened, the generally parallel elements 172 are pulled out of their parallel configuration, and the spaces 176 between adjacent (formerly) parallel elements 172 are enlarged, as depicted in FIG. 12C. Similar to previously described embodiments, resorbable material (not shown) may be inserted into the enlarged spaces 176 formed between the parallel elements 172 to thereby place the bridge 170 in an expanded state. When an implant incorporating the bridge 170 is inserted into a patient's body, the resorbable material is resorbed by the patient's body and the bridge 170 is transformed from the expanded state to a contracted state.

In additional to providing for lengthening of the bridge 170 (and hence of the implant), the undulating structure of the bridge 170 also allows the bridge 170 to bend and twist while still maintaining its structural integrity.

In a preferred embodiment, the bridge 170 is laser cut from a single piece of material, for example, nitinol. As shown in FIG. 12D, the bridge 170 may initially be formed as a flat structure (e.g., laser cut from a flat metal sheet) that is then bent or otherwise formed into the curved "C"-shaped cross-sectioned bridge 170 depicted in FIGS. 12A-12C. The step of bending or otherwise forming the bridge 170 into the curved shape could involve "setting" the curved shape into "memory" of the material, particularly where the bridge 170 is formed from a memory material such as Nitinol. Note, however, that bending or otherwise forming the bridge 170 into a curved "C"-shaped cross-sectional structure is optional; for example, the bridge 170 could be manufactured so that's its final shape prior to deployment is a generally flat shape such as that depicted in FIG. 12D.

An undulating bridge such as that depicted in FIGS. 12A-12D may be combined with various anchors, including spiral anchors, zig-zag anchors, or other anchor shapes and configurations known in the art. Furthermore, the anchors could be formed as a single construction with the undulating bridge 170, e.g., where the anchors and bridge are laser-cut from a single piece of tubing.

In yet another alternative embodiment of the invention, a bridge may be attached to one or both of the anchor portions using a coupling construction that allows substantially unrestrained movement between the bridge and anchor portion(s). For example, the bridge may be coupled to the anchor portions using suture, loops, or hinge mechanisms. Such coupling constructions can eliminate stress concentrations and thereby improve the overall strength of the implant structure. Such coupling constructions may be used for assembling a modular implant, wherein the bridge and anchor portions are manufactured separately and then later joined together. Modular construction of this type can provide the physician with more flexibility to select particular anchor and bridge sizes for a particular need.

Figure 13:
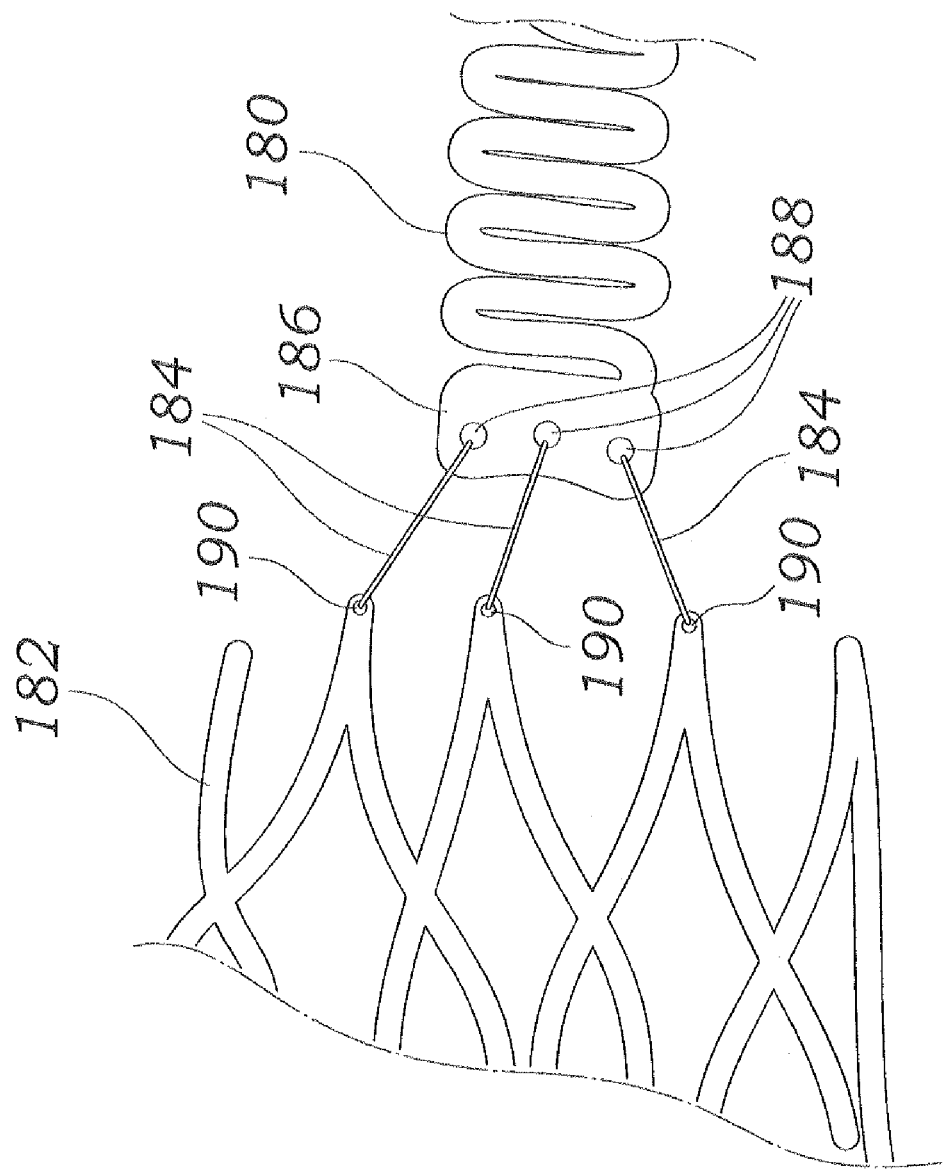
FIG. 13 is a side view of a bridge and anchor connected via suture according to an embodiment of the invention.

With reference now to FIG. 13, for purposes of illustration, a bridge 180 is connected to an anchor 182 via suture 184. The bridge 180 has an end 186 having three eyelets 188 through which one or more lines of suture 184 are passed. The anchor 182 includes a generally zig-zag body having three corresponding eyelets 190 through which the suture 184 is also passed. The suture 184 is then tied or otherwise secured so as to maintain the connection between the bridge 180 and anchor 182. However, the present invention is not limited to this configuration and may contain more or fewer eyelets on the bridge and/or anchor. Additionally, the implant does not need to have a one-to-one ratio of eyelets on the bridge to eyelets on the anchor. For instance, the bridge may only have two eyelets while the anchor may have three. Having a sutured connection between the bridge and the distal anchor can allow the implant increased flexibility to conform to the tortuous anatomy of the coronary sinus. For instance, with a sutured connector the bridge may be axially rotated about 180 degrees or more with respect to an anchor. As will be understood by one of ordinary skill in the art, the sutured connector may be placed between any implant bridge and corresponding distal or proximal anchors, such as those described in the present application.

Although exemplary implants have been described as having specific attributes, for example, specific numbers of coils, lengths, and diameters, it will be understood by those skilled in the art that modifications may be made to the described dimensions and other attributes of the implants while remaining within the scope and spirit of the claimed invention. Furthermore, the implants bridges contemplated herein may take a wide variety of alternative forms suitable for distributing stresses and should not be limited to the configurations described herein.

What is claimed is:

1. An apparatus for treating a mitral valve, comprising:
   an elongate member formed with a substantially spiral shape, the elongate member having a proximal end portion and a distal end portion;
   an expandable proximal anchor joined to the proximal end portion of the elongate member; and
   an expandable distal anchor joined to the distal end portion of the elongate member;
   wherein the elongate member is configured to adjust from an elongated state to a shortened state after delivery at least partially into a coronary sinus for reshaping a mitral annulus;
   wherein the elongate member comprises a plurality of coils and wherein one or more coils includes at least one window through which a resorbable material is threadable.

2. The apparatus of claim 1, wherein the plurality of coils have one or more spaces therebetween, and wherein a resorbable material is disposed within the spaces between adjacent coils for maintaining the elongate member in the elongated state.

3. An apparatus for treating a mitral valve, comprising:
   an elongate member formed with a substantially spiral shape, the elongate member having a proximal end portion and a distal end portion;
   an expandable proximal anchor joined to the proximal end portion of the elongate member; and
   an expandable distal anchor joined to the distal end portion of the elongate member;
   wherein the elongate member is configured to adjust from an elongated state to a shortened state after delivery at least partially into a coronary sinus for reshaping a mitral annulus;
   wherein the elongate member comprises two substantially parallel spiral members.

4. The apparatus of claim 3, wherein the two substantially parallel spiral members have one or more spaces therebetween, and wherein a resorbable material is disposed within the spaces between for maintaining the elongate member in the elongated state.

5. An apparatus for treating a mitral valve, comprising:
   an elongate member formed with a substantially spiral shape, the elongate member having a proximal end portion and a distal end portion;
   an expandable proximal anchor joined to the proximal end portion of the elongate member; and
   an expandable distal anchor joined to the distal end portion of the elongate member;
   wherein the elongate member is configured to adjust from an elongated state to a shortened state after delivery at least partially into a coronary sinus for reshaping a mitral annulus;
   wherein the elongate member has an undulating configuration, and wherein a resorbable material is disposed within spaces in the undulating configuration for maintaining the elongate member in the elongated state;
   wherein the elongate member has a substantially C-shaped cross section.

6. An apparatus for treating a mitral valve, comprising:
   an elongate member formed with a substantially spiral shape, the elongate member having a proximal end portion and a distal end portion;
   an expandable proximal anchor joined to the proximal end portion of the elongate member; and
   an expandable distal anchor joined to the distal end portion of the elongate member;
   wherein the elongate member is configured to adjust from an elongated state to a shortened state after delivery at least partially into a coronary sinus for reshaping a mitral annulus;
   wherein the proximal anchor and the distal anchor have a spiral shape.

7. An apparatus for treating a mitral valve, comprising:
an elongate member having a spiral shape, the elongate member having a proximal end portion and a distal end portion, wherein the elongate member comprises a plurality of coils;
an expandable proximal anchor joined to the proximal end portion of the elongate body; and
an expandable distal anchor joined to the distal end portion of the elongate body;
wherein the expandable proximal anchor and the expandable distal anchor are joined to the elongate body by sutures.

8. The apparatus of claim 7, wherein the elongate member comprises a memory material.

9. The apparatus of claim 7, wherein the elongate member is configured to adjust from an elongated state to a shortened state after delivery at least partially into a coronary sinus for reshaping a mitral annulus.

10. A method for treating a mitral valve using an implant, the implant including an elongate member having a spiral shape with coils, the elongate member having a proximal end portion and a distal end portion, an expandable proximal anchor joined to the proximal end portion of the elongate member, and an expandable distal anchor joined to the distal end portion of the elongate member, the method comprising:
inserting the implant at least partially into the coronary sinus;
expanding and anchoring the expandable distal anchor in the coronary sinus;
expanding and anchoring the expandable proximal anchor in or outside of the coronary sinus; and
after expanding and anchoring the expandable proximal and distal anchors, allowing resorption of resorbable material extending through openings in the coils, thereby causing the elongate member to change in length.

11. The method of claim 10, wherein the implant has resorbable material disposed within spaces between the coils to maintain the elongate member in an expanded state, and the method further comprises:
after expanding and anchoring the expandable distal anchor, and after expanding and anchoring the expandable proximal anchor, allowing the resorbable material to be resorbed, causing the elongate member to shorten and thereby reshape a mitral annulus.

12. The method of claim 10, further comprising:
after expanding and anchoring the expandable distal anchor, but before expanding and anchoring the expandable proximal anchor, retracting the expandable proximal anchor proximally with respect to the expandable distal anchor.

13. An apparatus for treating a patient, comprising:
an elongate member formed with a substantially spiral shape, the elongate member having a proximal end portion and a distal end portion;
an expandable proximal anchor joined to the proximal end portion of the elongate member; and
an expandable distal anchor joined to the distal end portion of the elongate member;
wherein the elongate member is configured to adjust from an elongated state to a shortened state after delivery at least partially into the patient;
wherein the elongate member comprises a plurality of coils and at least one opening in the plurality of coils through which a resorbable material is threadable.

14. The apparatus of claim 13, wherein the plurality of coils have one or more spaces therebetween, and wherein a resorbable material is disposed within the spaces between adjacent coils for maintaining the elongate member in the elongated state.

15. The apparatus of claim 14, further comprising a sheath covering the elongate member, the sheath maintaining the resorbable material in the spaces of the elongate member.

16. The apparatus of claim 13, wherein the apparatus is formed from a single piece of material.

17. The apparatus of claim 13, wherein the elongate member is made from shape memory material.

18. The apparatus of claim 17, wherein the shape memory material is nitinol.

19. The apparatus of claim 13, wherein the apparatus is sized to be inserted at least partially into the coronary sinus.

20. An apparatus for treating a patient, comprising:
an elongate member formed with a substantially spiral shape, the elongate member having a proximal end portion and a distal end portion;
an expandable proximal anchor joined to the proximal end portion of the elongate member and having a substantially spiral shape; and
an expandable distal anchor joined to the distal end portion of the elongate member and having a substantially spiral shape;
wherein the elongate member is configured to adjust from an elongated state to a shortened state after delivery at least partially into the patient.

21. The apparatus of claim 20, wherein the elongate member comprises a plurality of coils and wherein one or more coils.

22. The apparatus of claim 20, wherein the plurality of coils has one or more spaces therebetween, and wherein a resorbable material is disposed within the spaces between adjacent coils for maintaining the elongate member in the elongated state.

* * * * *